(12) United States Patent
Chen et al.

(10) Patent No.: US 9,273,095 B2
(45) Date of Patent: Mar. 1, 2016

(54) ANTIBIOTIC PEPTIDE AND PREPARATION METHOD THEREFOR AND APPLICATION THEREFOR

(75) Inventors: Yuxin Chen, Jiangsu (CN); Mingxia Chen, Jiangsu (CN); Yibing Huang, Jiangsu (CN); Yang Li, Jiangsu (CN); Yong Wang, Jiangsu (CN); Lili Qu, Jiangsu (CN); Wenren Wang, Jiangsu (CN)

(73) Assignee: Jiangsu Protelight Pharmaceutical & Biotechnology Co., Ltd., Jiangsu (CN)

( * ) Notice: Subject to any disclaimer, the term of this patent is extended or adjusted under 35 U.S.C. 154(b) by 0 days.

(21) Appl. No.: 14/112,064

(22) PCT Filed: Jan. 17, 2012

(86) PCT No.: PCT/CN2012/000079
§ 371 (c)(1),
(2), (4) Date: Oct. 16, 2013

(87) PCT Pub. No.: WO2012/142855
PCT Pub. Date: Oct. 26, 2012

(65) Prior Publication Data
US 2014/0329739 A1    Nov. 6, 2014

(30) Foreign Application Priority Data
Apr. 18, 2011 (CN) .......................... 2011 1 0095737

(51) Int. Cl.
*C07K 7/08* (2006.01)
*C07K 14/47* (2006.01)
*A61K 38/00* (2006.01)

(52) U.S. Cl.
CPC ............... *C07K 7/08* (2013.01); *C07K 14/4723* (2013.01); *A61K 38/00* (2013.01)

(58) Field of Classification Search
CPC ....... A61K 38/00; C07K 14/4723; C07K 7/08
See application file for complete search history.

(56) References Cited

FOREIGN PATENT DOCUMENTS

CN          102219831          10/2011

OTHER PUBLICATIONS

Seong-Cheol Park, Amphipathic α-helical peptide, HP (2-20), and its analogues derived from Helicobacter pylori: Pore formation mechanism in various lipid compositions, Biochimica et Biophysica Acta 1778 (2008) 229-241.*
Håvard Jenssen, Peptide Antimicrobial Agents, Clinical Microbiology Reviews, Jul. 2006, p. 491-511, vol. 19, No. 3.*

* cited by examiner

*Primary Examiner* — James H Alstrum Acevedo
*Assistant Examiner* — Erinne Dabkowski
(74) *Attorney, Agent, or Firm* — Hammer & Associates, P.C.

(57) ABSTRACT

Disclosed are an antibiotic peptide and the like, having an amino acid sequence of Ac-Phe-Lys-Lys-Leu-Lys-Lys-Leu-Phe-Ser-Lys-Leu-Trp-Asn-Trp-Lys-NH$_2$ (SEQ ID No:2). Also disclosed are a method of preparing the antibiotic peptide and the like, and the application thereof. The antibiotic peptide and the like synthesized by the solid phase synthetic technology according to the present invention can be used as a formulation against microbial infection and as alternate or adjuvant medicaments of antibiotics in the prior art.

8 Claims, 3 Drawing Sheets

PL-13: Ac-FKKLKKLFSKLWNWK-NH$_2$

SEQUENCE LISTING

```
<160> NUMBER OF SEQ ID NOS: 34

<210> SEQ ID NO 1
<211> LENGTH: 15
<212> TYPE: PRT
<213> ORGANISM: Artificial Sequence
<220> FEATURE:
<223> OTHER INFORMATION: PEPTIDE

<400> SEQUENCE: 1

Phe Lys Lys Leu Lys Lys Leu Phe Ser Lys Leu Trp Asn Trp Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: PEPTIDE

<400> SEQUENCE: 2

Phe Lys Arg Leu Glu Lys Leu Phe Ser Lys Ile Trp Asn Trp Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: PEPTIDE

<400> SEQUENCE: 3

Phe Lys Arg Leu Glu Lys Leu Phe Ser Lys Ile Trp Asn Trp Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: PEPTIDE

<400> SEQUENCE: 4

Phe Lys Lys Leu Lys Lys Lys Phe Ser Lys Leu Trp Asn Trp Lys
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: PEPTIDE

<400> SEQUENCE: 5
```

```
Phe Lys Lys Leu Lys Lys Arg Phe Ser Lys Leu Trp Asn Trp Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: PEPTIDE

<400> SEQUENCE: 6

Phe Lys Lys Leu Lys Lys Lys Phe Ser Lys Leu Trp Asn Trp Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: PEPTIDE

<400> SEQUENCE: 7

Phe Lys Lys Leu Lys Lys Arg Phe Ser Lys Leu Trp Asn Trp Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: PEPTIDE

<400> SEQUENCE: 8

Leu Lys Lys Leu Lys Lys Leu Leu Ser Lys Leu Trp Asn Trp Lys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: PEPTIDE

<400> SEQUENCE: 9

Phe Lys Lys Leu Lys Lys Leu Phe Ser Lys Leu Leu Asn Leu Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: PEPTIDE

<400> SEQUENCE: 10

Leu Lys Lys Leu Lys Lys Leu Phe Ser Lys Leu Leu Asn Leu Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: PEPTIDE

<400> SEQUENCE: 11
```

```
Leu Lys Lys Leu Lys Lys Leu Leu Ser Lys Leu Trp Asn Trp Lys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: PEPTIDE

<400> SEQUENCE: 12

Phe Lys Lys Leu Lys Lys Leu Phe Ser Lys Leu Leu Asn Leu Lys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: PEPTIDE

<400> SEQUENCE: 13

Leu Lys Lys Leu Lys Lys Leu Phe Ser Lys Leu Leu Asn Leu Lys
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: PEPTIDE

<400> SEQUENCE: 14

Phe Lys Lys Leu Lys Lys Leu Phe Ser Lys Leu Trp Asn
1               5                   10

<210> SEQ ID NO 15
<211> LENGTH: 13
<212> TYPE: PRT
<213> ORGANISM: Artificial Sequence
<220> FEATURE:
<223> OTHER INFORMATION: PEPTIDE

<400> SEQUENCE: 15

Lys Leu Lys Lys Leu Phe Ser Lys Leu Trp Asn Trp Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: PEPTIDE

<400> SEQUENCE: 16

Lys Lys Leu Lys Lys Leu Phe Ser Lys Leu Trp Asn Trp
1               5                   10

<210> SEQ ID NO 17
<211> LENGTH: 13
<212> TYPE: PRT
<213> ORGANISM: Artificial Sequence
<220> FEATURE:
<223> OTHER INFORMATION: PEPTIDE

<400> SEQUENCE: 17

Phe Lys Lys Leu Lys Lys Leu Phe Ser Lys Leu Trp Asn
```

<210> SEQ ID NO 18
<211> LENGTH: 13
<212> TYPE: PRT
<213> ORGANISM: Artificial Sequence
<220> FEATURE:
<223> OTHER INFORMATION: PEPTIDE

<400> SEQUENCE: 18

Lys Leu Lys Lys Leu Phe Ser Lys Leu Trp Asn Trp Lys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: PEPTIDE

<400> SEQUENCE: 19

Lys Lys Leu Lys Lys Leu Phe Ser Lys Leu Trp Asn Trp
1               5                   10

<210> SEQ ID NO 20
<211> LENGTH: 15
<212> TYPE: PRT
<213> ORGANISM: Artificial Sequence
<220> FEATURE:
<223> OTHER INFORMATION: PEPTIDE

<400> SEQUENCE: 20

Trp Lys Lys Leu Lys Lys Leu Phe Ser Lys Leu Trp Asn Phe Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: PEPTIDE

<400> SEQUENCE: 21

Phe Lys Lys Phe Lys Lys Leu Leu Ser Lys Leu Trp Asn Trp Lys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: PEPTIDE

<400> SEQUENCE: 22

Phe Lys Lys Leu Lys Lys Leu Phe Ser Lys Leu Lys Asn Trp Trp
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: PEPTIDE

<400> SEQUENCE: 23

Trp Lys Lys Leu Lys Lys Leu Phe Ser Lys Leu Trp Asn Phe Lys
1               5                   10                  15

```
<210> SEQ ID NO 24
<211> LENGTH: 15
<212> TYPE: PRT
<213> ORGANISM: Artificial Sequence
<220> FEATURE:
<223> OTHER INFORMATION: PEPTIDE

<400> SEQUENCE: 24

Phe Lys Lys Phe Lys Lys Leu Leu Ser Lys Leu Trp Asn Trp Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: PEPTIDE

<400> SEQUENCE: 25

Phe Lys Lys Leu Lys Lys Leu Phe Ser Lys Leu Lys Asn Trp Trp
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: PEPTIDE

<400> SEQUENCE: 26

Leu Phe Lys Lys Leu Lys Lys Leu Phe Ser Lys Leu Trp Asn Trp Lys
1               5                   10                  15

<210> SEQ ID NO 27
<211> LENGTH: 17
<212> TYPE: PRT
<213> ORGANISM: Artificial Sequence
<220> FEATURE:
<223> OTHER INFORMATION: PEPTIDE

<400> SEQUENCE: 27

Lys Leu Phe Lys Lys Leu Lys Lys Leu Phe Ser Lys Leu Trp Asn Trp
1               5                   10                  15

Lys

<210> SEQ ID NO 28
<211> LENGTH: 16
<212> TYPE: PRT
<213> ORGANISM: Artificial Sequence
<220> FEATURE:
<223> OTHER INFORMATION: PEPTIDE

<400> SEQUENCE: 28

Phe Lys Lys Leu Lys Lys Leu Phe Ser Lys Leu Trp Asn Trp Lys Lys
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: PEPTIDE

<400> SEQUENCE: 29

Phe Lys Lys Leu Lys Lys Leu Phe Ser Lys Leu Trp Asn Trp Lys Lys
```

```
                           1               5                  10                  15
Ser

<210> SEQ ID NO 30
<211> LENGTH: 16
<212> TYPE: PRT
<213> ORGANISM: Artificial Sequence
<220> FEATURE:
<223> OTHER INFORMATION: PEPTIDE

<400> SEQUENCE: 30

Leu Phe Lys Lys Leu Lys Lys Leu Phe Ser Lys Leu Trp Asn Trp Lys
  1               5                  10                  15

<210> SEQ ID NO 31
<211> LENGTH: 17
<212> TYPE: PRT
<213> ORGANISM: Artificial Sequence
<220> FEATURE:
<223> OTHER INFORMATION: PEPTIDE

<400> SEQUENCE: 31

Lys Leu Phe Lys Lys Leu Lys Lys Leu Phe Ser Lys Leu Trp Asn Trp
  1               5                  10                  15

Lys

<210> SEQ ID NO 32
<211> LENGTH: 16
<212> TYPE: PRT
<213> ORGANISM: Artificial Sequence
<220> FEATURE:
<223> OTHER INFORMATION: PEPTIDE

<400> SEQUENCE: 32

Phe Lys Lys Leu Lys Lys Leu Phe Ser Lys Leu Trp Asn Trp Lys Lys
  1               5                  10                  15

<210> SEQ ID NO 33
<211> LENGTH: 17
<212> TYPE: PRT
<213> ORGANISM: Artificial Sequence
<220> FEATURE:
<223> OTHER INFORMATION: PEPTIDE

<400> SEQUENCE: 33

Phe Lys Lys Leu Lys Lys Leu Phe Ser Lys Leu Trp Asn Trp Lys Lys
  1               5                  10                  15

Ser

<210> SEQ ID NO 34
<211> LENGTH: 18
<212> TYPE: PRT
<213> ORGANISM: Artificial Sequence
<220> FEATURE:
<223> OTHER INFORMATION: PEPTIDE

<400> SEQUENCE: 34

Glu Leu Glu Lys Gly Gly Leu Glu Gly Glu Lys Gly Gly Lys Glu Leu
  1               5                  10                  15

Glu Lys
```

ANTIBIOTIC PEPTIDE AND PREPARATION METHOD THEREFOR AND APPLICATION THEREFOR

FIELD OF TECHNOLOGY

The present invention belongs to the field of polypeptide technology, especially relates to a novel antimicrobial peptide and methods of making and using such peptide to prepare therapeutic compositions for inhibiting microbial infections.

PRIOR ART

Antibiotic, the medicine that resistant to pathogenic microorganisms, is the biggest class of antibacterial and anti-inflammatory medicine. Antibiotics, the substance produced by bacteria, fungi or other microorganisms in their life, with the ability to inhibit or kill pathogenic microorganisms like bacteria, fungi, spirochete, *mycoplasma*, and *chlamydia*, can cure illness. Other antibiotics are treatments for malignant tumors. Antibiotic drugs with numerous varieties are widely applied to different kinds of infectious illness. The extensive clinical use of classical antibiotics has led to the growing emergence of many medically relevant resistant strains of bacteria. Moreover, only three new structural classes of antibiotics (the oxazolidinone, linezolid, the streptogramins and the lipopeptide-daptomycin) have been introduced into medical practice in the past 40 years. Therefore, the development of a new class of antibiotics has great significance. The cationic antimicrobial peptides could represent such a new class of antibiotics. Although the exact mode of action of the cationic antimicrobial peptides has not been entirely established, all cationic amphipathic peptides interact with membranes and the cytoplasmic membrane is the main target of antimicrobial peptides, where antimicrobial peptide accumulation in the membrane may cause increased permeability and loss of barrier function. Therefore, the development of resistance to these membrane active peptides is almost impossible because this would require substantial changes in the lipid composition of cell membranes of microorganisms.

Two major classes of the cationic antimicrobial peptides are the α-helical and the β-sheet peptides. The β-sheet class includes cyclic peptides constrained in this conformation either by intramolecular disulfide bonds, e.g., defensins and protegrins, or by an N-terminal to C-terminal covalent bond, e.g., gramicidin S and tyrocidines. Unlike the β-sheet peptides, α-helical peptides are more linear molecules that mainly exist as disordered structures in aqueous media and become amphipathic helices upon interaction with the hydrophobic membranes, e.g., cecropins, magainins and melittins.

Nowadays, most antimicrobial peptides discovered are directly purified from organisms. Examples like Magainin from epidermis of toad and Melittin from body of bee all consist of L-amino acids.

The antimicrobial peptides directly obtained from organisms are exclusive to other organisms, therefore they can hardly be applied to human people. Namely this class of antimicrobial peptides is greatly harmful to human people. Many of the antimicrobial peptides are unable to become drugs because of this toxicity. In addition, some peptides consisting of L-amino acids are apt to be hydrolyzed to lose activity by protease, hence their effectiveness are severely restricted.

SUMMARY OF THE INVENTION

In the present invention, peptides which can be used as antimicrobial agents and related compounds are synthesized with solid phase peptide synthesis method. This solves increasingly severe drug resistance problem and takes away the suffering that refractory infection brings to the patients. The antimicrobial peptides in the present invention can be applied to all sorts of refractory infections and common infections. They would become a promising substitute or ancillary drug of existing antibiotics.

In order to achieve the objects described above in this invention, the following technologic methods are adopted:

The amino acid sequence of polypeptide mentioned in this invention which can be used as antimicrobial agents is Ac-Phe-Lys-Lys-Leu-Lys-Lys-Leu-Phe-Ser-Lys-Leu-Trp-Asn-Trp-Lys-NH$_2$(SEQ ID No. 1), including L-enantiomers (namely PL-13, SEQ ID NO: 1) and D-enantiomers (namely PL-18, SEQ ID NO: 1).

Preferably, said antimicrobial peptide wherein Leu in the amino acid sequence is substituted by any amino acid residues in Ile, Val, norleucine and norvaline.

Preferably, said antimicrobial peptide wherein Phe in the amino acid sequence is substituted by any amino acid residues in Trp, Tyr, Leu, Ile, Val, norleucine and norvaline.

Preferably, said antimicrobial peptide wherein Trp in the amino acid sequence is substituted by any amino acid residues in Phe, Tyr, Leu, Ile, Val, norleucine and norvaline.

Preferably, said antimicrobial peptide comprising whole L-enantiomers and whole D-enantiomers; or any one or several amino acids of said antimicrobial peptide are substituted by L-amino acid or D-amino acid.

Preferably, the peptide with amino acid sequence 85% to 100% homologous to said antimicrobial peptide and its related compounds generated by substitution of some amino acids with different methods, lengthening or truncation of peptide sequence.

This invention also provides a solid phase peptide synthesis method to synthesize said antimicrobial peptide of previous technologic method, including steps as follow:

1) Taking amides resin, Fmoc protected amino acid, coupling reagent and organic alkali as initial raw materials; the Fmoc protected amino acid-amide resin conjugate is prepared in protected organic solvent.

2) Solid phase method is utilized to couple sequentially connected amino acids comprising protecting groups one by one, and linear peptide with its side-chain totally protected is synthesized.

3) Last amino acid on N-terminal of peptide is connected to resin and Fmoc protecting groups are taken off, and proper chemical modification is carried out.

4) Shear reagent is added to shear off peptide from resin, and after vacuum freeze drying crude peptide is generated.

Preferably, that purified peptide is prepared on $C_4$, or C8, or $C_{18}$ reversed-phase chromatography column using HPLC linear AB gradient at a flow rate of 0.5-5 ml/min, wherein mobile phase A is 0.01-0.5% aqueous TFA, and B is 0.01-0.5% TFA in acetonitrile.

More preferably, the purity of peptide is verified by analytical RP-HPLC as described below: runs are performed on $C_4$, or C8, or $C_{18}$ column using AB gradient and a flow rate of 0.1-5 ml/min, wherein mobile phase A is 0.01-0.5% aqueous TFA, and B is 0.01-0.5% TFA in acetonitrile.

The antimicrobial peptides of the invention can be applied to prepare therapeutic composition for inhibiting microbial infection such as antibacterial agents. If made to antibacterial agents, herein the range of dosage of antimicrobial peptide in said antibacterial agent is: 0.1-50 mg/kg in injection, 0.1-50 mg/kg in oral liquid, 1/10000-10%/piece of externally-applied agents, 1/10000-10%/piece of eye drops, and 1/10000-1‰/piece of lotion.

The antimicrobial peptides of the invention have potent antimicrobial activities and are useful against bacteria, fungi, viruses, and protozoa. The peptides are generally effective in the context of any organism having a cellular or structural component of a lipid bilayer membrane. These peptides are effective compounds for uses in human and/or veterinary medicine, or as agents in agricultural, food science, or industrial applications.

From numerous structure and effectiveness studies on both natural and synthetic antimicrobial peptides, we discover that some physical characteristics are vital for antimicrobial activity. These characteristics are including suitable charge number under mild pH values, the presence of both hydrophobic and alkaline residues, an amphipathic nature that segregates basic and hydrophobic residues, and an inducible or pre-formed secondary structure (α-helical or β-sheet).

The present invention also provides an antimicrobial peptide comprising an amino acid sequence Ac-Phe-Lys-Lys-Leu-Lys-Lys-Leu-Phe-Ser-Lys-Leu-Trp-Asn-Trp-Lys-NH$_2$ (SEQ ID No. 1).

The present invention also provides a method of treating microbial infections comprising administering to the patient with an antimicrobial peptide compound of the invention. In clinical practice, the microbial infections involve infections caused by one or more pathogens like a bacterium, a virus, a fungus, or a protozoan, e.g., infection caused by two different kinds of bacteria, and so forth. However, clinical test is for the process of infection and determination of therapeutic plan, which is relatively cumbersome. This invention is aimed to treat infections caused by complicate and drug-resistant pathogens by one kind of administration (antimicrobial peptides).

This invention synthesizes PL-13 (SEQ ID NO: 1) and peptide analogs with the technology of solid phase peptide de novo design. These peptides possess potent antibacterial and antifungal activity, meanwhile low toxicity to human cells. In the composition of sequence, these peptides (can be composed of 13 to 17 homologous amino acids, shown in sequence listing information of Example 1) share amino acid homology higher than 85% with PL-13 (SEQ ID NO: 1).

The polypeptide molecule of this invention is in certain secondary structure (e.g. helical structure) in a hydrophobic environment. We have used circular dichroism (CD) spectroscopy to monitor α-helical structure in 50% trifluoroethanol (a mimic of the hydrophobic environment of the cytoplasmic membrane).

The preferred antimicrobial peptides of this invention that are helical analogs with potential biological activities have very little alpha-helical structure in benign medium (a non-denaturing medium like 50 mM PO$_4$ buffer containing 100 mM KCl, pH 7) monitored by circular dichroism spectroscopy. This structural property can have importance in mechanisms of antimicrobial peptides, for example: a) decreasing polymerization of molecule in benign medium, namely self-association ability; b) allowing the peptide to more easily penetrate through the cell wall to reach the membrane of the microbe. Furthermore, disruption of the α-helical structure in benign medium has no impacts on the attraction of peptide (positively-charged) to the cell wall surface (negatively-charged) of the microbe, but the lack of structure can decrease the affinity of peptide (hydrophobic interactions between hydrophobic groups in cell wall surface and hydrophobic surface of peptide) for this surface which allows the peptide to more easily pass through the cell wall and enter the interface region of the membrane where the peptide is parallel to the surface of membrane. Here the peptide can be induced by the hydrophobic environment of the membrane into its alpha-helical structure. In this alpha-helical structure, we hypothesize that the non-polar face of the peptide can interact with the hydrophobicity of the membrane, and its polar and positively-charged groups on the polar face can interact with the polar head of the phospholipids (negatively-charged) on the surface of the membrane.

An antimicrobial peptide is net positively-charged and amphipathic/amphiphilic when in an alpha-helical structure. For example, the alpha-helical peptide has a non-polar face or hydrophobic surface on one side of the molecule and a polar and positively-charged surface on the other side of the molecule; i.e., the molecule is amphipathic.

Certain peptide analogs are studied by temperature profiling in RP-HPLC from 5 to 80° C., to evaluate the self-associating ability of the molecules in solution. The ability to self-associate can be another important parameter in measuring peptide antimicrobial and hemolytic activities. It is generally found that a high ability to self-associate in solution is correlated with weak antimicrobial activity and strong hemolytic activity of the peptides. Biological studies showed that strong hemolytic activity of the peptides generally correlated with high hydrophobicity, high amphipathicity and high helicity. In most cases, the D-amino acid substituted peptides possess an enhanced average antimicrobial activity compared with L-diastereomers. By replacing the hydrophobic or hydrophilic amino acid residue on the non-polar or the polar face of these amphipathic molecules with a series of selected D- and L-amino acids, we further demonstrate that this method can be used for the rational design of other antimicrobial peptides with enhanced activities.

The preferred peptide PL-13 (SEQ ID NO: 1) and its D-enantiomers peptide PL-18 (SEQ ID NO: 1) of this invention comprise following amino acid sequence.

TABLE 1

| Peptide and amino acid sequence | | |
|---|---|---|
| Peptide name | Product sequence | One letter code sequence |
| PL-13 (SEQ ID NO: 1) | Ac-Phe-Lys-Lys-Leu-Lys-Lys-Leu-Phe-Ser-Lys-Leu-Trp-Asn-Trp-Lys-NH$_2$ | Ac-$F_L$-$K_L$-$K_L$-$L_L$-$K_L$-$K_L$-$L_L$-$F_L$-$S_L$-$K_L$-$L_L$-$W_L$-$N_L$-$W_L$-$K_L$-NH$_2$ |
| PL-18 (SEQ ID NO: 1) | D-Ac-Phe-Lys-Lys-Leu-Lys-Lys-Leu-Phe-Ser-Lys-Leu-Trp-Asn-Trp-Lys-NH$_2$ | Ac-$F_D$-$K_D$-$K_D$-$L_D$-$K_D$-$K_D$-$L_D$-$F_D$-$S_D$-$K_D$-$L_D$-$W_D$-$N_D$-$W_D$-$K_D$-NH$_2$ |

Here in one letter code, a subscript D following an amino acid residue denotes that the residue is a D-amino acid residue; similarly, a subscript L denotes an L-amino acid residue. In the peptide name, an initial D- (not subscripted) denotes all D-amino acids in the peptide except where specified. Ac denotes Nα-acetyl and NH$_2$ denotes Cα-amide.

Aforementioned antimicrobial peptide and its composition can be prepared as any medically biological carrier or agent to treat patients with infection.

The bulk drug of this invention preferred the dosage ranging from 0.01 to 50 mg.

The excipients used for preparation of injection of this invention include sdisodium ethylenediamine tetraacetic acid, Tween-80, mannitol, glycerol and propylene glycol.

The excipients used for preparation of oral solid agent of this invention include microcrystalline cellulose, L-HPC, polyvinylpyrrolidone, aerosol, starch, dextrin, sucrose, lactose, talcum powder, magnesium stearate, sodium carboxymethyl starch, PVPP, pregelatinized starch and so forth.

The excipients used for preparation of externally-applied agent of this invention include mannitol, Polysorbate 80, polyethylene glycol, Polyoxyl(40)Stearate, glycerol, carbomer, triethanolamine, alcohol, polyvinylpyrrolidone, tartaric acid, sodium bicarbonate, polyvinyl alcohol, sodium benzoate, microcrystalline cellulose, hydroxypropyl methylcellulose and so forth.

The excipients used for preparation of oral liquid agent of this invention include alcohol, ethylparaben, methyl hydroxybenzoate, Polysorbate 80, sodium benzoate, sorbic acid, honey, sucrose, sodium bisulfate, sodium thiosulfate, ascorbic acid, thiocarbamide, disodium EDTA, phosphoric acid, citric acid, glycerol, lactose and so forth.

Aforementioned raw material composition can be matched with proportional common medical excipients to make one kind of formulation comprising injection, tablets, capsules, granules, oral liquid, ointment, cream ointment, gel, eye drops, aerosol, patch, plastics, and lotion with conventional methods in this field. The preparation and technology of common formulations are shown in following examples.

The range of dosage of antimicrobial peptide in said antimicrobial agents is: 0.1-50 mg/kg in injection, 0.1-50 mg/kg in oral agents, 1/10000-10%/piece of externally-applied agents, 1/10000-10%/piece of eye drops, and 1/100000-1‰/piece of lotion.

BRIEF DESCRIPTION OF ACCOMPANYING DRAWINGS

DETAILED DESCRIPTION OF PREFERRED EMBODIMENTS

The invention may be further demonstrated by the following specific examples.

Example 1

Sequence Information of Related Antimicrobial Peptides Derived from PL-12 (SEQ ID NO: 2)

PL-12 (SEQ ID NO: 2), a 15-residue amphipathic α-helical antimicrobial peptide comprising the sequence Ac-FKRLEKLFSKIWNWK-NH$_2$ (SEQ ID NO: 2) with a polar and non-polar face, is selected as the native parent peptide in this study. Its polar face consists of 7 hydrophilic residues (three lysine residues, one arginine, one glutamate, one serine, and one asparagine) and one hydrophobic residue (one tryptophan). In contrast, the non-polar face consists of 6 hydrophobic residues (two leucines, one isoleucine, two phenylalanines, and one tryptophan) and one hydrophilic residue (one lysine).

Figure 1:
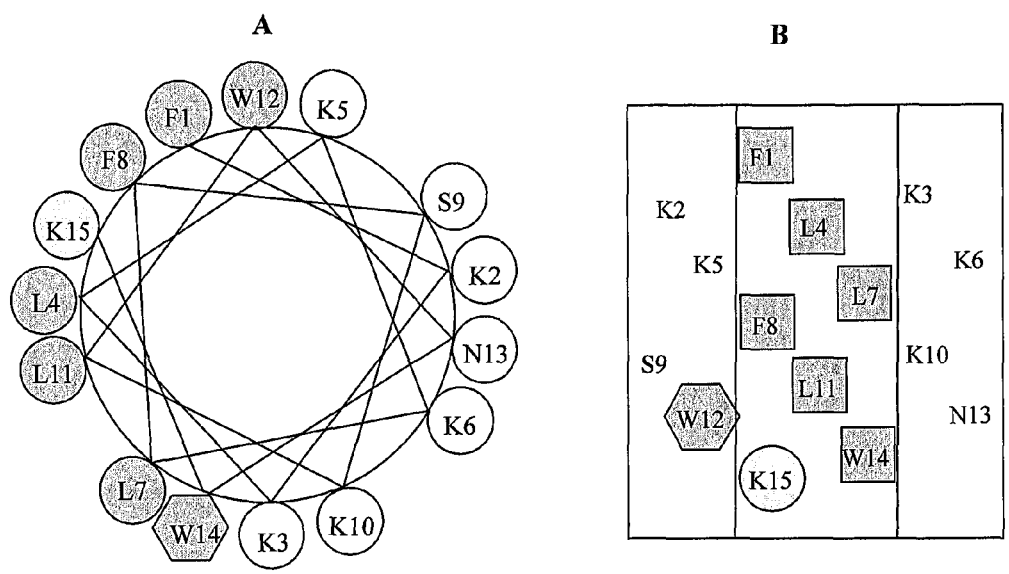
FIG. 1 illustrates PL-13 (SEQ ID NO: 1) as a helical wheel/nets and its amino acid sequences.

We obtain serial PL-13 (SEQ ID NO: 1) peptide analogs by means of substitution of amino acids (FIG. 1). FIG. 1 illustrates PL-13 (SEQ ID NO: 1) as a helical wheel/nets and its amino acid sequences. Shown are the residues on the non-polar/hydrophobic face (boxed residues) and hydrophilic residues on the non-polar/hydrophobic face (circled residues), and hydrophobic residues on the hydrophilic face (residues in hexagonal box). The hydrophilic face is indicated as an open arc, whilst the hydrophobic face is shown as a solid arc in the helical wheel. Ac denotes Nα-acetyl and NH$_2$ denotes Cα-amide. The amino acid residues are indicated by one-letter codes, based upon which we do further modification and get a group of related antimicrobial peptides with the same activity. Both PL-12 (SEQ ID NO: 2) and PL-13 (SEQ ID NO: 1) are composed of L-amino acid. We design enantiomers peptides PL-17 (SEQ ID NO: 3) and PL-18 (SEQ ID NO: 1) (both are composed of D-amino acid). Consequently, PL-17 (SEQ ID NO: 3) and PL-18 (SEQ ID NO: 1) are completely opposite to the corresponding PL-12 (SEQ ID NO: 2) and PL-13 (SEQ ID NO: 1) in stereochemistry.

PL-23 (SEQ ID NO: 4) and PL-24 (SEQ ID NO: 5) are two of the peptide analogs made based on different charged amino acid substitution. They are generated by varying the nature of the charged residue selected for substituting amino acids of sequence of PL-13 (SEQ ID NO: 1). The amino acid selected for substitution is preferably a charged amino acid and is in particular an amino acid with a net positive charge. The charged residues include Lys, Arg, Orn, His, diamino butyric acid and diamino propionic acid. We note that Orn has a delta/δ-amino group instead of an epsilon/ε-amino group in Lys, i.e., the side-chain is shorter by one carbon atom; diamino butyric acid is one carbon shorter than Orn; i.e., it has a gamma/γ-amino group; diamino propionic acid is two carbons shorter than Orn, i.e., it has a beta/β-amino group. PL-34 (SEQ ID NO: 6) and PL-35 (SEQ ID NO: 7) are D-enantiomers of above two peptides.

PL-25 to 27 (SEQ ID NOs: 8-10) are generated by multiple substitutions of PL-13 (SEQ ID NO: 1). The activity of a peptide with multiple substitutions (e.g. two substitutions) at different sites of invented peptide can still be effective. For a particular peptide generated by multiple substitutions, such multiple substitutions can be at least as effective as a single substitution in the center of the non-polar face. Considering the amino acid composition of peptide sequence and particularly the importance hydrophobic amino acid has in biological activity, we insist that the peptide sharing the percentage of similarity higher than 85% with PL-13 (SEQ ID NO: 1) in amino acid composition possesses great biological activity. PL-36 to 38 (SEQ ID NOs: 11-13) are enantiomers of above two peptides.

PL-28 to 30 (SEQ ID NOs: 14-16) are two peptides shorter than invented peptide generated by truncation of the N-terminal residue and C-terminal residue. This peptide generated by removing one or two residues of one terminal or two terminals of PL-13 (SEQ ID NO: 1), still keeps nearly the same antibacterial activity as PL-13 (SEQ ID NO: 1) in that it shares the percentage of similarity higher than 85% with PL-13 in amino acid composition. PL-39 to 41 (SEQ ID NOs: 17-19) are enantiomers of above two peptides.

The hydrophobic residues on the surface of peptides constitute overall hydrophobic face of peptides by hydrophobic interaction. The non-polar face of PL-13 (SEQ ID NO: 1) consists of F1, L4, L7, F8, L11, W14 and K15. Likewise, the polar face consists of K2, K3, K5, K6, S9, K10, W12 and N13. The amino acid residues constituting PL-13 (SEQ ID NO: 1) especially the hydrophobic residues are shuffled (shuffling of hydrophobic residues on non-polar face and polar residues on polar face, or shuffling of non-polar face residues or polar face residues that do not substantially change the amphipathicity of the molecule) wherein a resulting peptide is still biologically active. PL-31 to 33 (SEQ ID NOs: 10-22) are parts of sequence (any two residues are selected for site interchanging), and this kind of shuffling made PL-31 to 33 (SEQ ID NOs: 10-22) share 100% homology with PL-13 (SEQ ID NO: 1) in residue composition so that they have nearly the same antibacterial activity as PL-13 (SEQ ID NO: 1). PL-42 to 44 (SEQ ID NOs: 23-25) are enantiomers of above two peptides.

TABLE 2

Summary of partial sequence listing information.

| SEQ ID NO: | Peptide Name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| | Eantiomer A | L | L | L | L | L | L | L | L | L | L | L | L | L | L | L |
| 2 | PL-12 | F | K | R | L | E | K | L | F | S | K | I | W | N | W | K |
| 1 | PL-13 | F | K | K | L | K | K | L | F | S | K | L | W | N | W | K |
| 4 | PL-23 | F | K | K | L | K | K | K | F | S | K | L | W | N | W | K |
| 5 | PL-24 | F | K | K | L | K | K | R | F | S | K | L | W | N | W | K |
| 8 | PL-25 | L | K | K | L | K | K | L | L | S | K | L | W | N | W | K |
| 9 | PL-26 | F | K | K | L | K | K | L | F | S | K | L | L | N | L | K |
| 10 | PL-27 | L | K | K | L | K | K | L | F | S | K | L | L | N | L | K |
| 14 | PL-28 | F | K | K | L | K | K | L | F | S | K | L | W | N | | |
| 15 | PL-29 | | K | L | K | K | L | F | S | K | L | W | N | W | K | |
| 16 | PL-30 | | K | K | L | K | K | L | F | S | K | L | W | N | W | |
| 20 | PL-31 | W | K | K | L | K | K | L | F | S | K | L | W | N | F | K |
| 21 | PL-32 | F | K | K | F | K | K | L | L | S | K | L | W | N | W | K |
| 22 | PL-33 | F | K | K | L | K | K | L | F | S | K | L | K | N | W | W |
| | Eantiomer B | D | D | D | D | D | D | D | D | D | D | D | D | D | D | D |
| 3 | PL-17 | F | K | R | L | E | K | L | F | S | K | I | W | N | W | K |
| 1 | PL-18 | F | K | K | L | K | K | L | F | S | K | L | W | N | W | K |

TABLE 2-continued

Summary of partial sequence listing information.

| SEQ ID NO: | Peptide Name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| 6 | PL-34 | F | K | K | L | K | K | K | F | S | K | L | W | N | W | K |
| 7 | PL-35 | F | K | K | L | K | K | R | F | S | K | L | W | N | W | K |
| 11 | PL-36 | L | K | K | L | K | K | L | L | S | K | L | W | N | W | K |
| 12 | PL-37 | F | K | K | L | K | K | L | F | S | K | L | L | N | L | K |
| 13 | PL-38 | L | K | K | L | K | K | L | F | S | K | L | L | N | L | K |
| 17 | PL-39 | F | K | K | L | K | K | L | F | S | K | L | W | N | | |
| 18 | PL-40 | | K | L | K | K | L | F | S | K | L | W | N | W | K | |
| 19 | PL-41 | | K | K | L | K | K | L | F | S | K | L | W | N | W | |
| 23 | PL-42 | W | K | K | L | K | K | L | F | S | K | L | W | N | F | K |
| 24 | PL-43 | F | K | K | F | K | K | L | L | S | K | L | W | N | W | K |
| 25 | PL-44 | F | K | K | L | K | K | L | F | S | K | L | K | N | W | W |

Example 1-1

Peptide Analogs Generated by Lengthening PL-13 (SEQ ID NO: 1)

The peptide analogs in this invention are generated by adding one or two amino acid residues to N-terminal or C-terminal of peptides. PL-46 (SEQ ID NO: 26), generated by adding one hydrophobic residue to the hydrophobic face (N-terminal) of PL-13 (SEQ ID NO: 1), increased the hydrophobic face of peptide. And PL-47 (SEQ ID NO: 27) is generated by adding one hydrophilic residue to PL-46 (SEQ ID NO: 26). This change of length preserved over 85% amino acid similarity, and made peptide analogs possess similar biological activity with PL-13 (SEQ ID NO: 1).

TABLE 3

Peptide sequences generated by lengthening two terminals of PL-13

| Peptide Name | -2 | -1 | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|
| Eantiomer A | | | L | L | L | L | L | L | L | L | L | L | L | L | L | L | L | | |
| PL-13 (SEQ ID NO: 1) | | | F | K | K | L | K | K | L | F | S | K | L | W | N | W | K | | |
| PL-46 (SEQ ID NO: 26) | | L | F | K | K | L | K | K | L | F | S | K | L | W | N | W | K | | |
| PL-47 (SEQ ID NO: 27) | K | L | F | K | K | L | K | K | L | F | S | K | L | W | N | W | K | | |
| PL-48 (SEQ ID NO: 28) | | | F | K | K | L | K | K | L | F | S | K | L | W | N | W | K | K | |
| PL-49 (SEQ ID NO: 29) | | | F | K | K | L | K | K | L | F | S | K | L | W | N | W | K | K | S |
| Eantiomer B | | | D | D | D | D | D | D | D | D | D | D | D | D | D | D | D | | |
| PL-18 (SEQ ID NO: 1) | | | F | K | K | L | K | K | L | F | S | K | L | W | N | W | K | | |
| PL-51 (SEQ ID NO: 30) | | L | F | K | K | L | K | K | L | F | S | K | L | W | N | W | K | | |
| PL-52 (SEQ ID NO: 31) | K | L | F | K | K | L | K | K | L | F | S | K | L | W | N | W | K | | |

TABLE 3-continued

Peptide sequences generated by
lengthening two terminals of PL-13

| Peptide Name | Amino Acid Position | | | | | | | | | | | | | | | | | |
|---|---|---|---|---|---|---|---|---|---|---|---|---|---|---|---|---|---|---|
| | -2 | -1 | 1 | 2 | 3 | 4 | 5 | 6 | 7 | 8 | 9 | 10 | 11 | 12 | 13 | 14 | 15 | 16 | 17 |
| PL-53 (SEQ ID NO: 32) | | | F | K | K | L | K | K | L | F | S | K | L | W | N | W | K | K | |
| PL-54 (SEQ ID NO: 33) | | | F | K | K | L | K | K | L | F | S | K | L | W | N | W | K | K | S |

Example 1-2

Peptide Analogs with Similar Hydrophobic Substitutions

Further peptides of the invention are generated by making single substitutions of amino acid residues with relatively similar hydrophobicity. Single hydrophobicity substitutions with side-chains of similar hydrophobicity are generated and have biological activity.

TABLE 4

The amino acid residues used for substitutions of homologous amino acid

| Residues of PL-13 (SEQ ID NO: 1) | Substituted residues |
|---|---|
| Leu | Ile, Val, norleucine, norvaline |
| Phe | Trp, Tyr, Leu, Ile, Val, norleucine, norvaline |
| Trp | Phe, Tyr, Leu, Ile, Val, norleucine, norvaline |

Example 2

Preparation of PL-13 (SEQ ID NO: 1) and Related Antimicrobial Peptides and Test of Relevant Parameters All the peptides of this invention are generated by syntheses which are carried out by solid-phase peptide synthesis using Fmoc t-butyloxycarbonyl chemistry and MBHA (4-methylbenzhydrylamine) resin (0.97 mmol/g). However, it is understood in the art that there are other suitable peptide synthetic devices or that manual peptide synthesis could be carried out to produce the peptides of the present invention. The crude peptides are purified by preparative reversed-phase chromatography (RP-HPLC) using a Zorbax 300 SB-$C_8$ column (250×9.4 mm I.D.; 6.5 μm particle size, 300 Å pore size; Agilent Technologies) with a linear AB gradient (0.2% acetonitrile/min) at a flow rate of 2 ml/min, wherein mobile phase A is 0.1% aqueous TFA and B is 0.1% TFA in acetonitrile. The purity of peptides is verified by analytical RP-HPLC as described below. The peptides are further characterized by electrospray mass spectrometry and amino acid analysis.

Analytical RP-HPLC of Peptides—

Peptides are analyzed on an Agilent 1200 series liquid chromatograph (Little Falls, Del.). Runs are performed on a Zorbax 300 SB-C8 column (150×4.6 mm I.D.; 5 μm particle size, 300 Å pore size) from Agilent Technologies using linear AB gradient (1% acetonitrile/min) and a flow rate of 1 ml/min, where solvent A is 0.05% aqueous TFA, pH 2 and solvent B is 0.05% TFA in acetonitrile.

In the studies described hereinafter, the 15-residue peptide having the sequence Ac-FKRLEKLFSKIWNWK-NH$_2$ (PL-12, SEQ ID NO: 2) is utilized as the framework to study the effects of peptide hydrophobicity/hydrophilicity, amphipathicity and helicity by one or more amino acid substitutions on biological activities. These studies demonstrate i) the importance of the peptide self-association parameter in α-helical antimicrobial peptides; ii) that these substitutions enhance antimicrobial activity, decrease toxicity and improve antimicrobial specificity while maintaining broad spectrum activity for fungi, gram-negative and gram-positive bacteria.

Characterization of Helical Structure—

The mean residue molar ellipticities of peptides are determined by circular dichroism (CD) spectroscopy, using a Jasco J-720 spectropolarimeter (Jasco, Easton, Md.), at 25° C. under benign conditions (50 mM KH$_2$PO$_4$/K$_2$HPO$_4$/100 mM KCl, pH7), as well as in the presence of an α-helix inducing solvent, 2,2,2-trifluoroethanol (TFE) (50 mM KH$_2$PO$_4$/K$_2$HPO$_4$/100 mM KCL, pH 7 buffer/50% TFE). A 10-fold dilution of a 500 μM stock solution of the peptide is loaded into a 0.02 cm fused silica cell and its mean residue molar ellipticity scanned from 190 to 250 nm. The values of mean residue molar ellipticities of the peptide at a wavelength of 222 nm are used to estimate the relative amount of α-helicity of the peptides.

Figure 2:
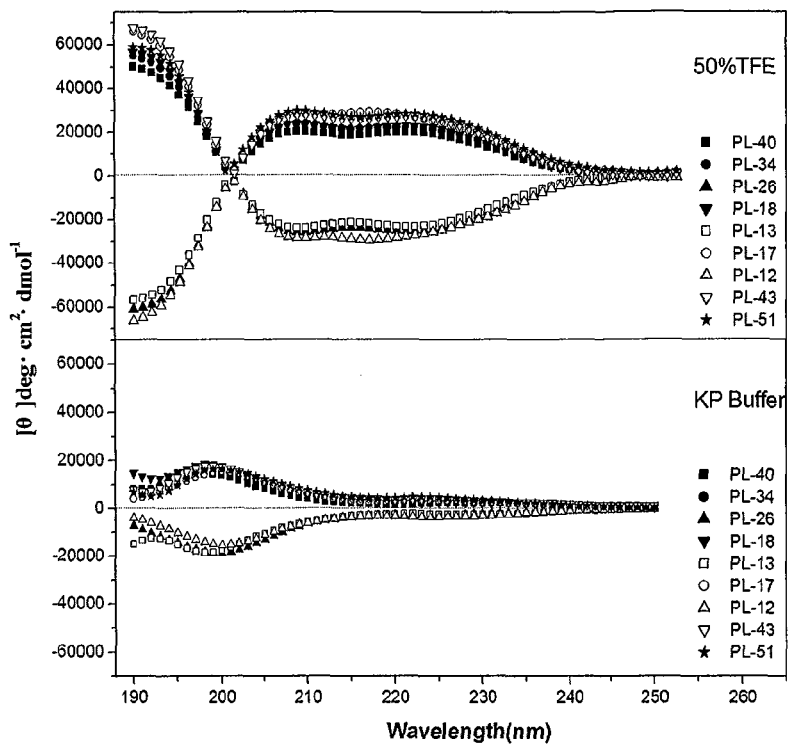
FIG. 2 illustrates graphical results of Circular dichroism (CD) spectra of peptide and its analogs.

To determine the secondary structure of peptides in different environments, circular dichroism (CD) spectra of the peptide analogs are measured under physiologically related pH and ionic strength (100 mM KCl, 50 mM aq. PO4, pH 7 referred to as benign conditions) and also in 50% TFE to mimic the hydrophobic environment of the membrane. CD spectra of the peptide analogs are measured under benign conditions (100 mM KCl, 50 mM KH$_2$PO$_4$/K$_2$HPO$_4$, pH 7, referred to as KP buffer) and also in 50% trifluoroethanol (TFE) to mimic the hydrophobic environment of the membrane. As shown in FIG. 2, the parent peptide, PL-12 (SEQ ID NO: 2), is only partially helical in KP buffer. However, in the presence of 50% TFE, all three L-peptides are fully folded α-helical structures with similar molar ellipticities and helicity. As expected, the D-peptides showed spectra that are exact mirror images compared to their L-enantiomers, with mean residue molar ellipticities equivalent but of opposite sign both in benign KP buffer and in 50% TFE (Table 5).

TABLE 5

Biophysical data of peptide analogs.

| Peptide [a] | Hydrophobicity [b] | | Benign buffer | | 50% TFE | |
|---|---|---|---|---|---|---|
| | $t_{R5}$(min) | $t_{R80}$(min) | $[\theta]_{222}$ [c] | % helix [d] | $[\theta]_{222}$ [c] | % helix [d] |
| PL-40 (SEQ ID NO: 18) | 33.16 | 30.94 | 1700 | 6.0 | 19950 | 70.7 |

TABLE 5-continued

Biophysical data of peptide analogs.

| Peptide [a] | Hydrophobicity [b] | | Benign buffer | | 50% TFE | |
| --- | --- | --- | --- | --- | --- | --- |
| | $t_{R5}$(min) | $t_{R80}$(min) | $[\theta]_{222}$[c] | % helix[d] | $[\theta]_{222}$[c] | % helix[d] |
| PL-34 (SEQ ID NO: 6) | 34.76 | 32.75 | 2350 | 8.3 | 22000 | 78.0 |
| PL-26 (SEQ ID NO: 9) | 35.66 | 33.49 | −2700 | 9.6 | −24650 | 87.4 |
| PL-18 (SEQ ID NO: 1) | 35.75 | 33.37 | 2300 | 8.2 | 22700 | 80.5 |
| PL-13 (SEQ ID NO: 1) | 35.75 | 33.37 | −2350 | 8.3 | −22750 | 80.7 |
| PL-17 (SEQ ID NO: 3) | 38.04 | 36.10 | 3400 | 12.1 | 26300 | 93.3 |
| PL-12 (SEQ ID NO: 2) | 38.04 | 36.10 | −3350 | 11.9 | −26450 | 93.8 |
| PL-43 (SEQ ID NO: 24) | 41.64 | 40.52 | 3950 | 14.0 | 27150 | 96.3 |
| PL-51 (SEQ ID NO: 30) | 42.59 | 41.35 | 4750 | 16.8 | 28200 | 100.0 |

[a] Amino acid sequences of peptides are shown in Table 2 and Table 3.
[b] Peptides are ordered by increasing hydrophobicity, i.e., by increasing retention time ($t_R$) in RP-HPLC at pH 2 at temperatures of 5° C.
[c] The mean residue molar ellipticities, $[\theta]222$, (deg·cm$^2$·dmol$^{-1}$) at wavelength 222 nm are measured at 25° C. in benign conditions (100 mM KCl, 50 mM PO$_4$, pH 7.0) or in buffer containing 50% TFE by circular dichroism spectroscopy. The negative values in mean residue molar ellipticity denote the right-handed helices and the positive values denote the left-handed helices.
[d] The helical content (in percentage) of a peptide relative to the mean residue molar ellipticity value (100%) of peptide PL-15 in the presence of 50% trifluoroethanol (TFE).

The CD spectra of peptide analogs are shown in FIG. 2.

FIG. 2 illustrates graphical results of Circular dichroism (CD) spectra of peptides at pH 7.4 and 25° C., in 50 mM aq. PO$_4$ containing 100 mM KCl, wherein KP buffer (50 mM KH$_2$PO$_4$, K$_2$HPO$_4$, 100 mM KCl, pH 7.4) mimics hydrophilic environment and KP buffer-TFE (1:1 [vol/vol]) mimics hydrophobic environment of cell membrane. The figure above represents the CD spectra of peptides in benign buffer without TFE, whilst the figure below represents CD spectra obtained in the presence of 50% TFE. The symbols used are: solid square for PL-40 (SEQ ID NO: 18), solid circle for PL-34 (SEQ ID NO: 6), solid upper triangle for PL-26 (SEQ ID NO: 9), solid lower triangle for PL-18 (SEQ ID NO: 1), open square for PL-13 (SEQ ID NO: 1), open circle for PL-17 (SEQ ID NO: 3), open upper triangle for PL-12 (SEQ ID NO: 2), open lower triangle for PL-43 (SEQ ID NO: 24), and solid pentagon for PL-51 (SEQ ID NO: 30).

RP-HPLC retention behavior has been frequently utilized to represent overall peptide hydrophobicity. It is well documented that the formation of a hydrophobic binding domain due to peptide secondary structure can affect peptide interactions with reversed-phase matrices, this effect having been observed especially for amphipathic α-helical peptides. Because of this preferred binding domain, amphipathic α-helical peptides are considerably more retentive than non-amphipathic peptides of the same amino acid composition. In addition, the chromatography conditions characteristic of RP-HPLC (hydrophobic stationary phase, non-polar eluting solvent) are able to induce and stabilize helical structure in potentially helical polypeptides in a manner similar to that of the helix-inducing solvent TFE. Thus, any differences in effective hydrophobicity via amino acid substitutions can be readily monitored through consequent differences in RP-HPLC retention time.

We further use temperature profiling during RP-HPLC to determine the self-association ability of various analogs of PL-13 (SEQ ID NO: 1) which would occur through interaction of the non-polar faces of these amphipathic peptides α-helices. We use 50% TFE aqueous acetonitrile and hydrophobic conditions in the reversed-phase column (hydrophobic stationary phase and the hydrophobic organic solvent in the mobile phase) since the hydrophobic environment of a reversed-phase column also could induce α-helical structure. Since its introduction, the technique of RP-HPLC temperature profiling has been applied on several types of molecules, including cyclic β-sheet peptides, monomeric α-helices and α-helices that dimerize, as well as α-helices that dimerize to form coiled-coils. Although peptides are eluted from a reversed-phase column mainly by an adsorption/desorption mechanism, even a peptide strongly bound to a hydrophobic stationary phase will partition between the matrix and the mobile phase when the acetonitrile content becomes high enough during gradient elution. In summary, the mechanism is based on four assumptions: (i) at low temperature, just as an amphipathic α-helical peptide is able to dimerize in aqueous solution (through its hydrophobic, non-polar face), it will dimerize in solution during partitioning in reversed-phase chromatography; (ii) at higher temperatures, the monomer-dimer equilibrium favors the monomer as the dimer is disrupted; (iii) at sufficiently high temperatures, only monomer is present in solution; and (iv) peptide is always bound in its monomeric helical form to the hydrophobic stationary phase, i.e., the dimer can only be present in solution and disruption of the dimer is required for rebinding to the RP-HPLC matrix.

A control peptide (peptide C) designed to exhibit negligible secondary structure, i.e., a random coil, is employed as a standard peptide for temperature profiling during RP-HPLC to monitor peptide dimerization. With the sequence of Ac-ELEKGGLEGEKGGKELEK-amide (SEQ ID NO: 34) clearly exhibited negligible secondary structure, this 18-residue peptide is even in the presence of the strong alpha-helix inducing properties of 50% trifluoroethanol (TFE) and at the low temperature of 5° C. ($[\theta]_{222}$=−3,950). Since peptide C is a monomeric random coil peptide in both aqueous and hydrophobic media, its retention behavior over the temperature range 5-80° C. represents only general temperature effects on peptide retention behavior, i.e., a linear decrease in peptide retention time with increasing temperature due to greater solute diffusivity and enhanced mass transfer between the stationary and mobile phases at higher temperatures. Thus, after normalization to the retention times of peptide C, the retention behavior of the peptides only represents peptide self-association ability. Note that the higher the PA value, the greater the self-association ability. The order of peptide self-association ability of the three pairs of peptide enantiomers is identical to the order of peptide hydrophobicity. Apart from the decrease in retention time due to the general temperature effects noted above, destruction of the α-helix will also occur with increasing temperature, resulting in reduced retention times as the peptides become increasingly random coils.

The retention time data for the peptides is shown in Table 6 which records retention times at 5° C., the maximal retention times and retention times at 80° C. during the temperature profiling. Temperatures of 5-80° C. are the lower and upper temperature limits of temperature profiling in RP-HPLC, representing polymerization of the peptides at 5° C. and the monomerization of peptides at 80° C. due to denaturation of peptides by high temperature and dissociation of the polymers. The maximal retention times represent the threshold points at which peptides totally transform from polymeric to monomeric form.

TABLE 6

Relative hydrophobicity and self-association ability of peptide analogs during RP-HPLC temperature profiling.

| Peptides[a] | $t_R$(min)[b] | | | $\Delta t_R$(X-Peptide C)(min)[c] | | $P_A$ (min)[d] |
|---|---|---|---|---|---|---|
| | 5° C. | Max | 80° C. | 5° C. | 80° C. | |
| PL-40 (SEQ ID NO: 18) | 33.16 | 33.16 | 30.94 | 10.60 | 11.01 | 0.55 |
| PL-34 (SEQ ID NO: 6) | 34.76 | 34.76 | 32.75 | 12.20 | 12.82 | 0.81 |
| PL-26 (SEQ ID NO: 9) | 35.66 | 35.66 | 33.49 | 13.10 | 13.56 | 0.68 |
| PL-13 (SEQ ID NO: 1) | 35.75 | 35.75 | 33.37 | 13.19 | 13.45 | 0.56 |
| PL-18 (SEQ ID NO: 1) | 35.75 | 35.75 | 33.37 | 13.19 | 13.45 | 0.56 |
| PL-17 (SEQ ID NO: 3) | 38.02 | 38.04 | 36.10 | 15.46 | 16.19 | 0.93 |
| PL-43 (SEQ ID NO: 24) | 41.64 | 41.97 | 40.52 | 19.08 | 20.60 | 1.65 |
| PL-51 (SEQ ID NO: 30) | 42.59 | 42.96 | 41.35 | 20.02 | 21.42 | 1.63 |
| C[f] | 22.56 | 22.56 | 19.91 | | | |

[a]denotes the retention times of different peptides measured by RP-HPLC at 5° C. and 80° C., and the maximal retention times of peptides during temperature changing.
[b]denotes the retention time difference of peptide compared with that of control peptide C at different temperatures (5° C. and 80° C.), representing the relative hydrophobicity of the peptide analogs.
[c]$P_A$ denotes the association parameter of each peptide during the RP-HPLC temperature profiling, which is the maximal retention time difference of (($t_R^t$-$t_R^5$ for peptide analogs) − ($t_R^t$-$t_R^5$ for control peptide C)) within the temperature range, and ($t_R^t$-$t_R^5$) is the retention time difference of a peptide at a specific temperature (t) compared with that at 5° C.
[d]Peptide C is a random coil control, the retention behavior of which during RP-HPLC can reflect variation of RP-HPLC system caused by temperature changing. It is used to rule out the effect that variation of chromatographic column condition caused by temperature changing has on the retention time of peptide. Hence only physical property change of peptides at different temperatures is reflected.

The ability of the D-peptides to self-associate is determined by RP-HPLC temperature profiling. As expected, L- and D-peptide enantiomers are identical in behavior characteristics over this temperature range, because of the adoption of identical secondary structure, identical hydrophobic face and identical hydrophobic property on interacting with the reversed-phase matrix.

Elution times during RP-HPLC have frequently been utilized as a measure of relative hydrophobicity of peptide analogs. Thus, the retention time data in Table 6 can be considered to reflect the hydrophobicity difference among peptide analogs. The retention time data of peptide analogs in Table 6 are compared with that of the native peptide PL-13 (SEQ ID NO: 1) at 5° C. and 80° C. respectively so as to more easily visualize the variation in hydrophobicity of the peptide analogs.

Figure 3:
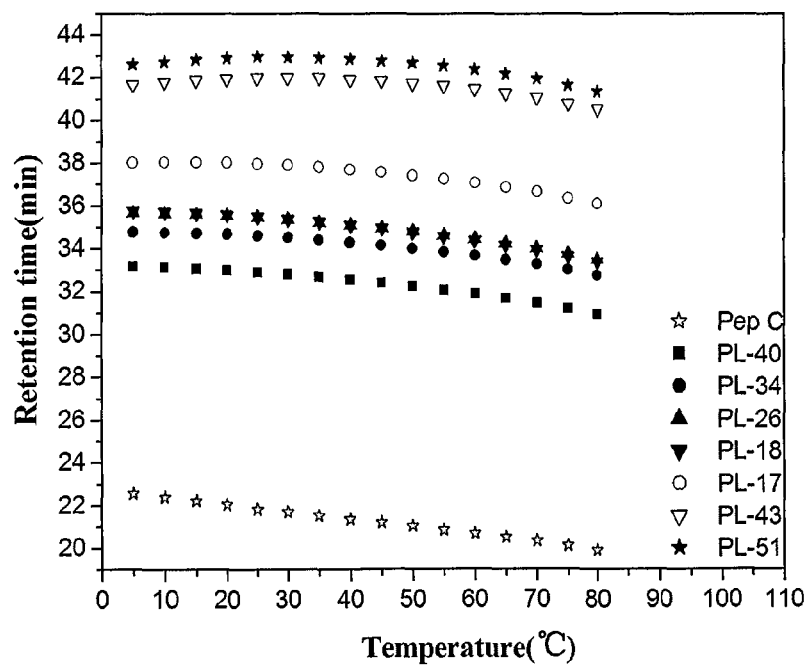
FIG. 3 illustrates the RP-HPLC temperature profiles of peptide and its analogs.

FIG. 3 shows the changing retention time profiles of peptides during RP-HPLC from 5° C. to 80° C. As mentioned above, the self-association of peptides is temperature-dependent. Peptides exist in a dynamic equilibrium of mutual transformation between polymer and monomer during RP-HPLC partitioning. At low temperatures, peptides tend to exist as dimmer or polymer (self-association). Generally self-association occurs with hydrophobic interaction of hydrophobic face of peptides, which weakens the combining ability of polymer and hydrophobic stationary phase, resulting in low retention time. With the increase of temperature, equilibrium of mutual transformation between polymer and monomer is shifted toward the monomeric form. The higher solution concentration of monomer during partitioning increases the on-rate for combination of peptide and chromatographic column, and the retention time therefore increases. It should be noted that the increased temperature also introduces other general effects on retention time because of lower mobile phase viscosity and a significant increase in mass transfer between the stationary phase and mobile phase. These effects decrease retention time with increasing temperature in a linear fashion, as shown for the retention time of random coil control peptide C. Conversely, for the polymerized peptides, at a given temperature polymers are disrupted and converted to monomers, and since combining ability of monomers and hydrophobic stationary phase is strong, the retention time reaches the maximal value. Above this critical temperature, one will observe a decrease in retention time of peptides with increasing temperature because of the low mobile phase viscosity, the increase in mass transfer and denaturation of peptide molecules caused by high temperature. The retention behavior of the random coil peptide standard C introduced by temperature profiling in RP-HPLC is utilized to reflect the variation of chromatographic column condition while temperature is varying. In this way the effect that variation of chromatographic column condition has on the retention behavior of peptide is ruled out. The data from retention time of peptides at every temperature spots in FIG. 3 minusing that at 5° C. are normalized relative to the temperature profile of the random coil peptide standard C, and normalized to the retention time at 5° C., the latter of which is presented as a dotted line in FIG. 4.

Figure 4:
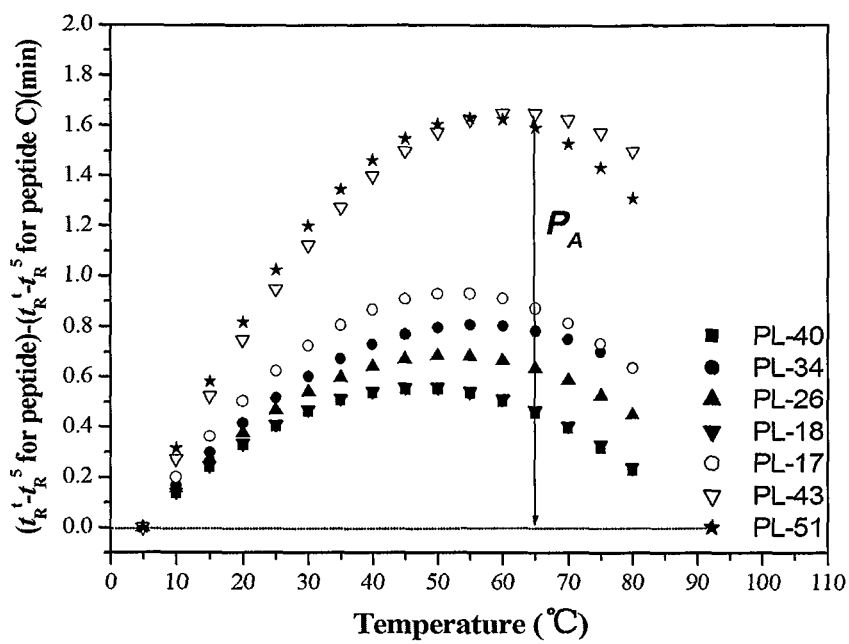
FIG. 4 illustrates the normalized RP-HPLC temperature profiles of peptide and its analogs.

It is observed that the peptide analogs in this study showed dramatic varying self-association ability in solution (FIG. 4). The maximal values of the change of retention times (($t_R^t$-$t_R^5$ for peptide)−($t_R^t$-$t_R^5$ for peptide C)) in FIG. 4 are defined as the peptide self-association parameter (PA) to quantify the association ability of peptide analogs in solution.

FIG. 3 illustrates the RP-HPLC temperature profiles of antimicrobial peptide and its analogs. Conditions: RP-HPLC, Agilent Zorbax 300 SB-$C_8$ column (150×4.6-mm 5-μm, 300-Å), 1% linear gradient elution at a flow-rate of 1 ml/min, where eluent A is 0.1% aqueous TFA and eluent B is 0.1% TFA in acetonitrile. A control peptide (peptide C), a random coil, is employed as a standard peptide. Retention data has been collected in 5° C. increments within the temperature range from 5° C. to 80° C. The symbols used are: solid square for PL-40 (SEQ ID NO: 18), solid circle for PL-34 (SEQ ID NO: 6), solid upper triangle for PL-26 (SEQ ID NO: 9), solid lower triangle for PL-18 (SEQ ID NO: 1), open circle for PL-17 (SEQ ID NO: 3), open lower triangle for PL-43 (SEQ ID NO: 24), solid pentagon for PL-51 (SEQ ID NO: 30), and open pentagon for peptide C.

FIG. 4 illustrates the normalized RP-HPLC temperature profiles of antimicrobial peptide and its analogs. Temperature profiles normalized to retention behavior of random coil peptide C1. Column and conditions: see FIG. 3. The retention behavior of the peptides is normalized to that of the random coil peptide C1 through the expression ($t_R^t$-$t_R^5$ for peptides) minus ($t_R^t$-$t_R^5$ for C1), which is defined as PA, i.e., the peptide self-aggregation ability. $t_R^t$ represents the retention times at a specific temperature of an antimicrobial peptide or the random coil peptide, and $t_R^5$ represents the retention times at 5° C. The symbols used are: solid square for PL-40 (SEQ ID NO: 18), solid circle for PL-34 (SEQ ID NO: 6), solid upper triangle for PL-26 (SEQ ID NO: 9), solid lower triangle for PL-18 (SEQ ID NO: 1), open circle for PL-17 (SEQ ID NO: 3), open lower triangle for PL-43 (SEQ ID NO: 24), solid pentagon for PL-51 (SEQ ID NO: 30), and dotted-line for peptide C.

Example 3

Sensitivity Test of PL-13 (SEQ ID NO: 1) and Related Serial Antimicrobial Peptide Antifungal Drugs 1. Experimental Bacteria Strains
   (1) Test strains: *monilia albicans* (*candida albicans*), *candida glabrata, candida krusei, candida tropicalis, aspergillus fumigatus* and *flavous*.

(2) Quality control strains: *candida krusei* JLC30366 (ATCC6258).

2. Reagents

Potato Dextrose Agar Medium (PDA) from Difco Company.

Potato Dextrose Broth Medium (PDB) from Difco Company.

RPMI-1640 liquid medium from Gibco BRL Company.

3-N-Morpholino propanesulfonic acid (MOPS) from Baiao Biology Co., LTD.

3. Antifungal Drugs

Antimicrobial peptides PL-13 (SEQ ID NO: 1) under test are supplied by Jiangsu ProteLight Pharmaceutical & Biotechnology Co., LTD. Both the control drug Fluconazol (FCZ) (purchased from Shanghai Sanwei Pharmaceutical Corporation) and Itraconazole (ICZ) (purchased from SIGMA) are standard powder with the purity higher than 99%.

4. Experimental Procedure (1) The bacterial strains which preserved on PDA slant are respectively inoculated onto PDA plate and slant medium. Activation of bacterial strains is conducted at a humidity level of 60% and 25° C. (for *aspergillus*) or 37° C. (for *candida*).

(2) 0.9% stroke-physiological saline solution comprising 0.5% Tween-80 is used to prepare bacterial suspension for experiment. Hemocytometer is utilized to adjust concentration of the bacterial suspension to $1-3\times10^6$ CFU/ml (0.5 McFarland units) to make stock solution in reserve at $-20°$ C. During the sensitivity test, the RPMI-1640 liquid medium is diluted 1000 times to $1-3\times10^3$ CFU/ml.

(3) The RPMI-1640 liquid is utilized as diluent to 10-fold dilute stock solution of peptides. According to the result of preliminary experiments, the initial concentration of peptides is set to 64 µg/ml and the terminal concentration is set to 0.125 µg/ml, with the concentration decreasing from the first orifice to the tenth orifice. 100 µl bacterial suspension is added to each orifice of former 11 orifices except the twelfth one with the concentration of $0.5-1.5\times10^3$ CFU/ml. The eleventh orifice is used as living control orifice, while the twelfth one as blank control.

(4) The RPMI-1640 liquid is utilized as diluent to 10-fold dilute stock solution of FCZ and ICZ. The initial concentration of FCZ is set to 64 µg/ml and the terminal concentration is set to 0.125 µg/ml, and the concentration of ICZ is set to 16 µg/ml with the terminal concentration set to 0.03 µg/ml. Ditto for other operations.

5. Results

The antifungal results of kinds of peptides are shown in Table 7.

TABLE 7

Minimal inhibitory concentration of kinds of peptides under test (µg/ml)

| | SEQ ID NO. | JLC 30366 *candida krusei* | JLC 30383 *candida krusei* | JLC 31379 *candida tropicalis* | JLC 31384 *candida tropicalis* | JLC 33659 *candida albicans* | JLC 33660 *candida albicans* |
|---|---|---|---|---|---|---|---|
| FCZ | | 16 | 8 | 0.5 | 0.25 | 0.25 | 0.25 |
| ICZ | | 0.25 | 0.25 | 0.03 | 0.03 | 0.03 | 0.0625 |
| PL-12 | 2 | 8 | 16 | 4 | 8 | 16 | 16 |
| PL-13 | 1 | 2 | 4 | 2 | 4 | 8 | 8 |
| PL-23 | 4 | 4 | 8 | 2 | 8 | 16 | 16 |
| PL-26 | 9 | 8 | 8 | 4 | 8 | 32 | 16 |
| PL-30 | 16 | 4 | 8 | 2 | 8 | 16 | 16 |
| PL-32 | 21 | 4 | 16 | 2 | 32 | 16 | 32 |
| PL-17 | 3 | 8 | 8 | 2 | 2 | 4 | 4 |
| PL-18 | 1 | 4 | 4 | 2 | 2 | 4 | 4 |
| PL-34 | 6 | 8 | 8 | 4 | 4 | 16 | 16 |
| PL-37 | 12 | 8 | 4 | 4 | 8 | 32 | 16 |
| PL-40 | 18 | 4 | 8 | 2 | 8 | 16 | 16 |
| PL-43 | 24 | 4 | 8 | 2 | 8 | 16 | 4 |
| PL-48 | 28 | 2 | 8 | 8 | 8 | 32 | 16 |
| PL-51 | 30 | 8 | 16 | 4 | 16 | 32 | 16 |

| | SEQ ID NO. | JLC 31512 *candida glabrata* | JLC 30367 *candida glabrata* | JLC 30506 *aspergillus fumigatus* | JLC 30883 *aspergillus fumigatus* | JLC 30784 *aspergillus flavous* | JLC 40437 *aspergillus flavous* |
|---|---|---|---|---|---|---|---|
| FCZ | | 1 | 2 | >64 | >64 | >64 | >64 |
| ICZ | | 0.03 | 0.0625 | 0.125 | 0.125 | 0.125 | 0.125 |
| PL-12 | 2 | 32 | 32 | 32 | 32 | >64 | >64 |
| PL-13 | 1 | 8 | 4 | 32 | 32 | >64 | >64 |
| PL-23 | 4 | 32 | 32 | 64 | 64 | >64 | >64 |
| PL-26 | 9 | 32 | 16 | 32 | 32 | >64 | >64 |
| PL-30 | 16 | 32 | 32 | 64 | 32 | >64 | >64 |
| PL-32 | 21 | 32 | 32 | 64 | 64 | >64 | >64 |
| PL-17 | 3 | 8 | 4 | 32 | 32 | >64 | >64 |
| PL-18 | 1 | 4 | 4 | 16 | 16 | >64 | >64 |
| PL-34 | 6 | 32 | 32 | >64 | >64 | >64 | >64 |
| PL-37 | 12 | 16 | 32 | 32 | 16 | >64 | >64 |
| PL-40 | 18 | 32 | 8 | 64 | 32 | >64 | >64 |
| PL-43 | 24 | 32 | 32 | 64 | 64 | >64 | >64 |
| PL-48 | 28 | 16 | 32 | 32 | 32 | >64 | >64 |
| PL-51 | 30 | 32 | 16 | 32 | 64 | >64 | >64 |

This experiment shows antimicrobial peptides above have higher inhibitory action on *Candida Mycoderma*, while lower inhibitory action on *Aspergillus Fumigatus*.

Example 4

Sensitivity Test of PL-13 (SEQ ID NO: 1) and Related Antimicrobial Peptides Series 1. Experimental Strains The experimental strains are 37 standard strains preserved in lab and clinical isolated bacteria, including drug-resistant bacteria and quality-control bacteria selecting *Staphylococcus aureus* ATCC29213, *Enterococcus faecalis* ATCC29212, *Escherichia coli* ATCC25922, *Pseudomonas aeruginosa* ATCC27853 and *klebsiella pneumoniae* ATCC700603.

2. Culture Medium

MH agar culture medium is purchased from National Institutes for Food and Drug Control. The MH bouillon culture-medium and brain-heart infusion medium are the products of American DIFCO Company.

3. Drugs

Antimicrobial peptides PL-13 (SEQ ID NO: 1) under test are supplied by Jiangsu ProteLight Pharmaceutical & Biotechnology Co., LTD.

As a control, levofloxacin is standard substance from National Institutes for Food and Drug Control 4. Experimental Procedure (1) Sensitivity test is conducted with two-fold agar dilution method and Denlay multipoint inoculator. Test bacteria are cultured with nutrient broth and brain heart infusion.

(2) The drug is double diluted into different concentration with MH broth after dissolved and then placed in the plate respectively.

(3) After dissolved, MH agar culture medium are injected into the plate with drug quantitatively and mixed to make the final concentration of drug are 0.03, 0.06, 0.125, . . . , 128 µg/ml respectively.

(4) After solidification of the culture medium in the plate, test bacteria ($10^4$ CFU/point) are inoculated by multipoint inoculator and cultured for 18 hours at constant 35° C. Then observe the results.

(5) The lowest concentration of the drug in the plate which showed no bacterial growth is the minimal inhibitory concentration (MIC).

5. Results

The antimicrobial activity of PL-13 (SEQ ID NO: 1) samples and the control medicine Levofloxacin against 37 bacteria strains are shown in Table 7. As shown herein, antimicrobial peptides like PL-13 (SEQ ID NO: 1) and positive control Levofloxacin have the same sterilizing effect on common susceptible bacteria. But for drug resistant bacteria, antimicrobial peptides show superior sterilizing efficiency.

TABLE 8

The MIC of different polypeptides under test (µM)

| Bacterial strains | SEQ ID NO. | | | | | | | | Levofloxacin |
|---|---|---|---|---|---|---|---|---|---|
| | 2 PL-12 | 1 PL-13 | 9 PL-26 | 6 PL-34 | 3 PL-17 | 1 PL-18 | 6 PL-34 | 24 PL-43 | |
| *Staphylococcus aureus* ATCC29213 | 1.3 | 0.7 | 1.3 | 0.7 | 0.3 | 0.7 | 2.6 | 1.3 | 0.60 |
| *Staphylococcus aureus* ATCC25923 | 1.3 | 0.7 | 1.3 | 0.7 | 0.3 | 0.7 | 2.6 | 1.3 | 0.30 |
| 15 | 1.3 | 0.7 | 1.3 | 0.7 | 0.3 | 0.7 | 2.6 | 1.3 | 0.30 |
| 08-49(MSSA) Meticillin susceptible *staphylococcus aureus* | 0.7 | 2.7 | 1.3 | 1.3 | 0.7 | 0.7 | 5.3 | 0.3 | 0.30 |
| 08-52(MRSA) Methicillin-resistant *staphylococcus aureus* | 1.3 | 2.7 | 1.3 | 0.7 | 5.3 | 2.7 | 3.3 | 3.3 | 76.92 |
| (MRSE) Methicillin-resistant *Staphylococcus epidermidis* ATCC12228 | 1.3 | 0.3 | 0.7 | 1.3 | 1.0 | 0.7 | 1.3 | 0.3 | 0.30 |
| 08-17 (MSSE) Meticillin susceptible *staphylococcus epidermidis* | 2.7 | 1.3 | 2.7 | 1.7 | 1.0 | 0.7 | 1.3 | 1.7 | 1.20 |
| 08-18 (MRSE) Methicillin-resistant *staphylococcus epidermidis* | 1.3 | 0.7 | 2.7 | 6.7 | 1.0 | 0.7 | 1.3 | 6.7 | 55.49 |
| *Enterococcus faecalis* ATCC29212 | 1.3 | 5.3 | 5.3 | 0.3 | 5.3 | 5.3 | 1.7 | 1.7 | 1.20 |
| HH22* (AMEs) Aminoglycoside-modifying enzyme | 0.3 | 1.7 | 6.7 | 0.3 | 10.7 | 1.7 | 0.3 | 0.3 | 1.20 |
| 06-7 | 5.3 | 1.3 | 5.3 | 6.7 | 5.3 | 2.7 | 21.3 | 10.67 | 19.23 |
| 06-71 (VRE) Vancomycin-resistant Enterococci | 0.3 | 1.7 | 1.7 | 1.3 | 1.7 | 1.3 | 1.3 | 0.7 | 2.40 |
| *Enterococcus faecium* 06-1 | 5.3 | 5.3 | 1.3 | 1.3 | 10.7 | 5.3 | 1.3 | 6.7 | 2.40 |
| 06-12 (VREF) Vancomycin-resistant enterococci | 1.3 | 5.3 | 5.3 | 0.3 | 1.7 | 5.3 | 0.7 | 1.7 | 2.40 |
| *Escherichia coli* ATCC 25922 | 0.03 | 0.03 | 0.3 | 0.3 | 0.2 | 1.3 | 0.1 | 0.03 | 0.14 |
| 08-5 (ESBLs) Extended Spectyumβ-lactamase | 1.3 | 0.7 | 1.3 | 1.7 | 0.3 | 1.3 | 5.3 | 6.7 | 76.92 |
| 26 | 1.3 | 0.7 | 0.7 | 1.3 | 0.3 | <0.08 | 2.7 | 6.7 | <0.7 |
| 272(TEM-88) | 0.7 | 0.3 | 1.3 | 6.7 | 0.3 | <0.08 | 1.3 | 1.7 | <0.7 |
| 274 (TEM-15) | 1.3 | 0.3 | 1.3 | 0.3 | 0.3 | 0.08 | 2.7 | 0.3 | 0.2 |
| 276 (TEM-52) | 1.3 | 0.7 | 0.7 | 0.03 | 0.7 | <0.08 | 2.7 | 0.3 | <0.2 |
| *Pseudomonas aeruginosa* TCC27853 | 5.3 | 1.3 | 5.3 | 0.3 | 1.3 | 0.3 | 1.7 | 0.3 | 1.20 |
| 17 | 2.7 | 1.3 | 1.7 | 0.3 | 2.7 | 0.2 | 1.3 | 1.7 | 0.7 |

TABLE 8-continued

The MIC of different polypeptides under test (μM)

| | SEQ ID NO. | | | | | | | | |
|---|---|---|---|---|---|---|---|---|---|
| | 2 | 1 | 9 | 6 | 3 | 1 | 6 | 24 | |
| Bacterial strains | PL-12 | PL-13 | PL-26 | PL-34 | PL-17 | PL-18 | PL-34 | PL-43 | Levofloxacin |
| *klebsiella pneumoniae* ATCC700603 | 2.7 | 0.7 | 5.3 | 0.7 | 2.7 | 0.3 | 2.7 | 0.3 | 1.2 |
| 08-2 (ESBLs) | 5.3 | 0.7 | 1.3 | 6.7 | 0.3 | 2.7 | 10.7 | 5.3 | 76.92 |
| 7 | 5.3 | 1.3 | 2.7 | 6.7 | 0.3 | <0.04 | 5.3 | 5.3 | <16 |
| *Enterobacter cloacae* 45301 | 0.3 | 1.3 | 1.7 | 0.3 | 1.3 | 0.04 | 1.3 | 0.03 | 0.1 |
| *Acinetobacter calcoaceticus*25001 | 0.03 | .3 | 6.7 | 1.3 | 1.3 | 1.7 | 1.3 | 0.3 | 0.1 |
| *Enterobacter aerogenes* 45102 | 0.03 | 2.7 | 1.3 | 0.3 | 1.3 | 0.04 | 0.03 | 0.003 | <0.02 |
| *Serratia marcescens* 41002 | 0.03 | 0.3 | 0.02 | 0.02 | 1.3 | 0.04 | 0.7 | 0.3 | 0.1 |
| *Shigella sonnei* strains 51592 | 2.7 | 0.7 | 1.3 | 0.04 | 0.3 | 0.04 | 2.7 | 0.3 | 0.1 |
| *Shigella* | 1.7 | 0.7 | 0.3 | 0.7 | 0.3 | 1.3 | <0.01 | 1.7 | <0.02 |
| *Shigella flexneri* | 2.7 | 0.7 | 1.3 | 0.3 | 0.3 | 0.0 | 2.7 | 0.7 | 0.1 |
| *Salmonella typhimurium* | 5.3 | 1.3 | 5.3 | 0.3 | 1.3 | 0.3 | 5.3 | 0.3 | <0.02 |
| Typhoid *bacillus* H901 | 5.3 | 1.3 | 2.7 | 0.3 | 0.7 | 0.3 | 5.3 | 0.7 | <0.02 |
| Feilaoti *citrobacter* 48001 | 5.3 | 1.3 | 2.7 | 1.7 | 2.7 | 0.3 | 1.3 | 0.3 | 0.1 |
| *Proteus vulgaris* 56 | 0.3 | 0.3 | 6.7 | 1.7 | 5.3 | 5.3 | 1.3 | 0.3 | <0.007 |

Example 5

Results of Hemolytic Activity Test of PL-13 (SEQ ID NO: 1)

1. Experimental Procedure (1) Samples are serial diluted with sterile PBS to 1000, 500, 250, 125, 64, 32, 16, 8, 4 μg/ml in turn and spread in 96-well plates, 100 μl per orifice.

(2) We use distilled water as positive control, sterile PBS as negative control and blank orifice with 200 μl PBS solution added. Each concentration above is made in triplicate.

(3) We take 3 ml whole blood from healthy volunteers and washed it with sterile PBS three times to prepare fresh 2% concentration red cell suspension. Then we added 100 μl red cell suspension into each orifice and made them cultured for 4 hours at 37° C. in the incubator. After centrifuged by plate-swashing centrifuge, the supernatant liquid is collected and measured absorbancy (OD value) at a wavelength of 570 nm. Then we compared the hemolytic efficiency of these concentrations.

(4) According to the documents standard, OD value which is higher than 0.1 is hemolytic concentration.

2. Results

Results of hemolytic activity test of PL-13 (SEQ ID NO: 1) and other antimicrobial peptides (shown in Table 9)

TABLE 9

Results of hemolytic activity test of polypeptides under test (n = 3)

| | | SEQ ID NO. | | | | | |
|---|---|---|---|---|---|---|---|
| Concentration of antimicrobial | | 1 | 3 | 9 | 6 | | |
| peptides (μg/ml) | positive | PL-13 | PL-17 | PL-26 | PL-34 | negative | blank |
| 1000 | 0.416 | 0.310 | 0.339 | 0.327 | 0.317 | 0.093 | 0.059 |
| 500 | 0.406 | 0.220 | 0.152 | 0.121 | 0.135 | 0.074 | 0.037 |
| 250 | 0.402 | 0.184 | 0.082 | 0.089 | 0.087 | 0.070 | 0.052 |
| 125 | 0.400 | 0.117 | 0.078 | 0.075 | 0.073 | 0.077 | 0.053 |
| 62.5 | 0.394 | 0.090 | 0.065 | 0.068 | 0.061 | 0.077 | 0.059 |
| 31.25 | 0.392 | 0.065 | 0.063 | 0.057 | 0.054 | 0.071 | 0.044 |
| 15.625 | 0.380 | 0.059 | 0.056 | 0.047 | 0.041 | 0.088 | 0.047 |
| 7.8125 | 0.371 | 0.043 | 0.033 | 0.020 | 0.032 | 0.071 | 0.044 |

The results show that antimicrobial peptides PL-13, 17, 26, 34 (SEQ ID NOs: 1, 3, 9, 6) almost have the same hemolysis rate, which demonstrated that all the dosage forms referred in the present invention have little hemolytic toxicity and therefore they have a light future of development.

Example 6

Anti-Infection Test of PL-13/PL-18 (SEQ ID NOs: 1/1) External-Applied Agent on Skin 1. Experimental Strains: *Staphylococcus epidermidis* ATCC12228 and *Staphylococcus aureus* ATCC25923

2. Experimental System

There are 50 male ICR mice with the weight of 20±2 g. According to their weight, they are randomly divided into 5 groups of 10 mice: negative infected control group, Bactroban positive control group, 1% concentration cream group, 1‰ concentration cream group and blank ground substance group. Each group is raised in the same plastic case. Their blank parts, heads, necks, backs and tails are marked with picric acid marking method. All the mice are raised with ordinary animal feeds in the ordinary animal houses and they could drink water freely. Alternating of light and dark is conducted every 12 hours.

3. Externally-Applied Agent on Skin

There are preparation of 1% concentration, 1‰ concentration, and blank ground substance preparation (supplied by Jiangsu ProteLight Pharmaceutical & Biotechnology Co., LTD.) and Bactroban (supplied by SK&F).

4. Experimental Procedure (1) The bacteria strains which preserved in liquid nitrogen are inoculated to MHB plate and cultured overnight at 37° C.

(2) The solid strains are inoculated to MHB liquid medium and overnight cultured shakily at the speed of 220 rpm at 37° C.

(3) The bacterial suspension cultured overnight is diluted to $5 \times 10^6$ CFU/ml and applied in reserve.

(4) Skin modeling: Mice's back are sheared and depilated by depilatory paste. After the hair off, they are abraded with 0.3 mm-long sandpaper to bleeding and injected 0.1 ml bacterial suspension with the concentration of $5 \times 10^6$ CFU/ml subcutaneously.

(5) Administration: All the groups except the negative infected control group are respectively applied different cream with the dosage of 0.1 ml once respectively in the morning and evening for 7 days.

(6) After 7 days, the visceral organs, blood and infected skin of mice are collected by aseptic method to count viable bacteria.

5. Results

Results of viable count of the visceral organs and blood are shown in Table 10-11.

TABLE 10

The effect PL-13/18 (SEQ ID NOs: 1/1) externally-applied agent takes on skin infection caused by *Staphylococcus aureus* ATCC25923 (CFU/plate n = 10)

| Groups | Number of animals | Whole blood | Skin (1:10) | Liver (1:5) | Spleen (1:5) |
|---|---|---|---|---|---|
| Infected control | 10 | 304 | 35925 | 157 | 70 |
| Bactroban | 10 | 12 | 1032 | 12 | 16 |
| 1% PL-13 (SEQ ID NO: 1) | 10 | 8 | 852 | 10 | 6 |
| 1‰ PL-13 (SEQ ID NO: 1) | 10 | 11 | 1005 | 12 | 14 |
| 1% PL-18 (SEQ ID NO: 1) | 10 | 16 | 997 | 9 | 8 |
| 1‰ PL-18 (SEQ ID NO: 1) | 10 | 12 | 1051 | 11 | 15 |
| Blank ground substance control | 10 | 224 | 25280 | 121 | 27 |

TABLE 11

The effect PL-13/18 (SEQ ID NOs: 1/1) externally-applied agent takes on skin infection caused by *Staphylococcus epidermidis* ATCC12228 (CFU/plate n = 10)

| Groups | Number of animal | Whole blood | Skin (1:10) | Liver (1:5) | Spleen (1:5) |
|---|---|---|---|---|---|
| Infected control | 10 | 129 | 10762 | 87 | 34 |
| Bactroban | 10 | 28 | 439 | 23 | 15 |
| 1% PL-13 (SEQ ID NO: 1) | 10 | 10 | 369 | 12 | 5 |
| 1‰ PL-13 (SEQ ID NO: 1) | 10 | 18 | 425 | 10 | 17 |
| 1% PL-18 (SEQ ID NO: 1) | 10 | 16 | 276 | 17 | 5 |
| 1‰ PL-18 (SEQ ID NO: 1) | 10 | 19 | 425 | 8 | 13 |
| Blank ground substance control | 10 | 94 | 9802 | 50 | 30 |

All the results mentioned above indicate that PL-13 (SEQ ID NO: 1) and PL-18 (SEQ ID NO: 1) externally-applied agent are effective at inhibiting against skin infection caused by *Staphylococcus aureus* and *Staphylococcus epidermidis*.

Example 7

Therapeutic Test of PL-18 (SEQ ID NO: 1) Injection on Animals with Generalized Infection 1. Experimental Animals There are 30 male and 30 female ICR mice with the weight ranging from 18 g to 22 g. According to their weight, they are randomly divided into 6 groups of 10 mice: blank control group, negative control group, Levofloxacin positive control group, PL-13 (SEQ ID NO: 1) high dose group, PL-13 (SEQ ID NO: 1) middle dose group and PL-13 (SEQ ID NO: 1) low dose group. Each group is raised in the same plastic case. With trinitrophenal marking method, all the mice are raised with ordinary animal feeds in the ordinary animal houses and they can drink water freely. Alternating of light and dark is conducted every 12 hours.

2. Infected Strains: *Pseudomonas aeruginosa* and *Staphylococcus aureus*

3. Anti-Infection Drug

PL-18 (SEQ ID NO: 1) freeze-dried powder injections (supplied by Jiangsu ProteLight Pharmaceutical & Biotechnology Co., LTD.), Levofloxacin Hydrochloride and Sodium Chloride Injection (supplied by Yangtze River Pharmaceutical Group) and 0.9% Sodium Chloride Injection (supplied by Chifeng Rongjitang Pharmaceutical CO., Ltd.)

4. Experimental Procedure (1) The preparation of bacterial suspension is the same as above.

(2) The *Pseudomonas aeruginosa* suspension cultured overnight is diluted to $1 \times 10^9$ CFU/ml. The *Staphylococcus aureus* suspension cultured overnight is diluted to $1 \times 10^8$ CFU/ml. They are all applied in reserve.

(3) Except the blank control group, every other mouse is injected with 0.2 ml *Pseudomonas aeruginosa* suspension with the concentration of $1 \times 10^9$ CFU/ml or 0.2 ml *Staphylococcus aureus* suspension with the concentration of $1 \times 10^8$ CFU/ml intraperitoneally to make model.

(4) Administration: Inject the drugs according to weight right after the model is ready. All the groups excepting the blank and the negative infected group are injected with different dosage of different injections through caudal vena twice a day successively for three days, and they are observed for fourteen days.

(5) Observe death of the animals and record their survival time.

5. Experimental Results

Effects of PL-18 (SEQ ID NO: 1) injection on survival time of mice with systemic infection of *Pseudomonas aeruginosa* and *Staphylococcus aureus* are shown in Tables 12-13.

TABLE 12

The effect of PL-18 (SEQ ID NO: 1) injection on survival time of mice with systemic infection of *Pseudomonas aeruginosa* (n = 10)

| Groups | Number of animals | Drugs | Dosage (mg/kg) | Mortality of mice in different days after infection | | | | | Mean survival Time (day) |
|---|---|---|---|---|---|---|---|---|---|
| | | | | 1 | 2 | 3 | 4 | 5 | |
| Blank control | 10 | normal saline | — | 0 | 0 | 0 | 0 | 0 | — |
| Negative control | 10 | — | — | 6 | 4 | 0 | 0 | 0 | 1.4 |
| Levofloxacin | 10 | ofloxacin | 30 | 4 | 2 | 0 | 0 | 0 | 6.4** |
| PL-18(high) (SEQ ID NO: 15) | 10 | PL-18 (SEQ ID NO: 1) | 5 | 0 | 1 | 2 | 2 | 0 | 8.6** |
| PL-18(middle) (SEQ ID NO: 15) | 10 | PL-18 (SEQ ID NO: 1) | 1 | 0 | 1 | 2 | 2 | 1 | 7.7** |
| PL-18(low) (SEQ ID NO: 15) | 10 | PL-18 (SEQ ID NO: 1) | 0.2 | 0 | 2 | 1 | 2 | 2 | 6.7** |

TABLE 13

The effect of PL-18 (SEQ ID NO: 1) injection on survival time of mice with systemic infection of *Staphylococcus aureus* (n = 10)

| Groups | Number of animals | Drugs | Dosage (mg/kg) | Mortality of mice in different days after infection | | | | | Mean survival Time (day) |
|---|---|---|---|---|---|---|---|---|---|
| | | | | 1 | 2 | 3 | 4 | 5 | |
| Blank control | 10 | normal saline | — | 0 | 0 | 0 | 0 | 0 | — |
| Negative control | 10 | — | — | 7 | 3 | 0 | 0 | 0 | 1.3 |
| Levofloxacin | 10 | ofloxacin | 30 | 5 | 2 | 0 | 0 | 0 | 5.4** |
| PL-18(high) (SEQ ID NO: 15) | 10 | PL-18 (SEQ ID NO: 1) | 5 | 0 | 1 | 1 | 1 | 2 | 9.9** |
| PL-18(middle) (SEQ ID NO: 15) | 10 | PL-18 (SEQ ID NO: 1) | 1 | 1 | 2 | 1 | 1 | 1 | 7.3** |
| PL-18(low) (SEQ ID NO: 15) | 10 | PL-18 (SEQ ID NO: 1) | 0.2 | 1 | 2 | 1 | 2 | 1 | 6.3** |

Note:
comparing with negative control group
*P < 0.05,
**P < 0.01

It is known from Tables 12 and 13 that until end of the experiment, mean survival days of mice among high, middle and low dose of PL-18 (SEQ ID NO: 1) control group and Levofloxacin positive control and negative control group are significantly different (p<0.01). This illustrates that anti-infection effect of high, middle and low dose of PL-18 (SEQ ID NO: 1) are all very good. Compared with Levofloxain control group, PL-18 (SEQ ID NO: 1) group is superior to positive control group obviously.

Example 8

Therapeutic Test of PL-34 (SEQ ID NO: 6) Oral Preparations on Animals with Systemic Infection 1. Experimental Animals There are 30 male and 30 female ICR mice with the weight ranging from 18 g to 22 g. According to their weight, they are randomly divided into 6 groups of 10 mice: Tinidazole positive control group, three PL-34 (SEQ ID NO: 6) groups, negative control group, and blank control group. The PL-34 (SEQ ID NO: 6) reagent groups are high, middle and low dose group. With trinitrophenal marking method, all the mice are raised with ordinary animal feeds in the ordinary animal houses and they can drink water freely. Alternating of light and dark is conducted every 12 hours.

2. Infected Strains: *Escherichia* and *Bacillus dysenteriae*

3. Anti-Infective Drugs

PL-34 (SEQ ID NO: 6) oral preparation (provided by Jiangysu ProteLight Pharmaceutical and Biotechnology Co., Ltd.), Tinidazole (Shandong Lukang Pharmaceutical Group Saite Co., Ltd.), 0.9% Sodium Chloride Injection (supplied by Chifeng Rongjitang Pharmaceutical CO., Ltd.)

4. Experimental Procedure (1) The preparation of bacterial suspension is the same as above.

(2) The *Escherichia* suspension cultured overnight is diluted to $1 \times 10^7$ CFU/ml. The *Bacillus dysenteriae* suspension cultured overnight is diluted to $1 \times 10^5$ CFU/ml. They are all applied in reserve.

(3) Except the blank control group, every other mouse is injected with 0.2 ml *Escherichia* suspension with the concentration of $1 \times 10^7$ CFU/ml or 0.2 ml *Bacillus dysenteriae* suspension with the concentration of $1 \times 10^5$ CFU/ml intraperitoneally to make model.

(4) Administration: The drugs are administered according to mice' weight right after the model is ready. All the groups excepting the blank and the infected negative control groups are administered by gavaging with different dosage of drugs three times a day successively for seven days, and they are observed for fourteen days.

(5) Observe death of the animals and record their survival time.

5. Experimental Results

Experimental results of PL-34 (SEQ ID NO: 6) tablet takes on survival time of the mice with systemic infection of *Escherichia* and *Bacillus dysenteriae*. (Tables 14-15)

TABLE 14

Effect of PL-34 (SEQ ID NO: 6) tablet takes on survival time of the mice with systemic infection of *Escherichia* (n = 10)

| Groups | Number of animals | Drugs | Dosage (mg/kg) | Mortality of mice in different days after infection | | | | | | Mean survival time (day) |
|---|---|---|---|---|---|---|---|---|---|---|
| | | | | 4 | 5 | 6 | 7 | 8 | 9 | |
| Blank control | 10 | normal saline | — | 0 | 0 | 0 | 0 | 0 | 0 | — |
| Negative control | 10 | — | — | 1 | 2 | 2 | 3 | 1 | 1 | 6.4 |
| Tinidazole | 10 | Tinidazole | 80 | 1 | 2 | 2 | 1 | 1 | 2 | 7.5* |
| PL-34(high) (SEQ ID NO: 16) | 10 | PL-34 (SEQ ID NO: 6) | 30 | 0 | 2 | 1 | 0 | 1 | 1 | 10.3** |
| PL-34(middle) (SEQ ID NO: 16) | 10 | PL-34 (SEQ ID NO: 6) | 10 | 0 | 2 | 2 | 1 | 1 | 1 | 8.8** |
| PL-34(low) (SEQ ID NO: 16) | 10 | PL-34 (SEQ ID NO: 6) | 3 | 1 | 1 | 2 | 1 | 2 | 2 | 7.6* |

TABLE 15

Effect of PL-34 (SEQ ID NO: 6) tablet takes on survival time of the mice with systemic infection of *Bacillus dysenteria*(n = 10)

| Groups | Number of animals | Drugs | Dosage (mg/kg) | Mortality of mice in different days after infection | | | | | | Mean survival time (day) |
|---|---|---|---|---|---|---|---|---|---|---|
| | | | | 4 | 5 | 6 | 7 | 8 | 9 | |
| Blank control | 10 | normal saline | — | 0 | 0 | 0 | 0 | 0 | 0 | — |
| Negative control | 10 | — | — | 2 | 2 | 2 | 3 | 1 | 0 | 5.9 |
| Tinidazole | 10 | Tinidazole | 80 | 2 | 1 | 2 | 2 | 1 | 1 | 7.0* |
| PL-34(high) (SEQ ID NO: 16) | 10 | PL-34 (SEQ ID NO: 6) | 30 | 1 | 1 | 2 | 2 | 2 | 1 | 7.4* |
| PL-34(middle) (SEQ ID NO: 16) | 10 | PL-34 (SEQ ID NO: 6) | 10 | 1 | 2 | 2 | 1 | 1 | 0 | 8.3** |
| PL-34(low) (SEQ ID NO: 16) | 10 | PL-34 (SEQ ID NO: 6) | 3 | 1 | 2 | 2 | 2 | 1 | 1 | 7.1* |

Note:
Comparing with negative control group
*$P < 0.05$.
**Comparing with negative control group
**$P < 0.01$.

It is known from Tabes 14 and 15 that until end of the experiment, average survival days of the mice are apparently different among all PL-34 (SEQ ID NO: 6) dose groups, Tinidazole positive control group and negative control group ($p<0.01$ or $0.05$). This demonstrates that PL-34 (SEQ ID NO: 6) oral preparation has better curative effect on mice against *Escherichia* and dysentery *bacillus* infection.

Example 9

Therapeutic Experiment of PL-18 (SEQ ID NO: 1) Injection on Animals with Multiple Mixed Infections 1. Experimental Animal:

There are 60 male and 60 female ICR mice with the weight ranging from 18 g to 22 g. According to their weight, they are randomly divided into 6 groups of 20 mice: blank control group, negative control group, Levofloxacin positive control group, and high, middle and low dose of PL-18 (SEQ ID NO: 1) group. With trinitrophenal marking method, all the mice are raised with ordinary animal feeds in the ordinary animal houses and they can drink water freely. Alternating of light and dark is conducted every 12 hours.

2. Infected Strains: *Candida albicans* and *Escherichia*

3. Anti-Infection Drugs

PL-18 (SEQ ID NO: 1) freeze-dried powder injection (supplied by Jiangsu ProteLight Pharmaceutical & Biotechnology Co., LTD.), Levofloxacin Hydrochloride and Sodium Chloride Injection (supplied by Yangtze River Pharmaceutical Group) and 0.9% Sodium Chloride Injection (supplied by Chifeng Rongjitang Pharmaceutical CO., Ltd.)

4. Experimental Procedure (1) The preparation of bacterial suspension is the same as above.

(2) The *Candida albicans* suspension cultured overnight is diluted to $1\times10^6$CFU/ml with Sodium Chloride and $5\times10^5$CFU of which is injected into abdominal cavity of every mouse; the *Escherichia* suspension cultured overnight is diluted to $2\times10^8$CFU/ml and $1\times10^7$CFU of which is injected into abdominal cavity of every mouse to make model with mixed infections.

(3) The blank control group is injected with normal saline into their abdominal cavity, the positive control group is injected with Levofloxacin into their abdominal cavity.

(4) Administration: The drugs are administered according to weight right after the model is ready. All the groups except the blank and the infected negative control group are injected with different dosage of different injections through caudal vena twice a day successively for three days, and they are observed for fourteen days.

(5) Observe death of the animals and record their survival time.

5. Experimental Result

Experimental result of PL-18 (SEQ ID NO: 1) injection takes on survival time of the mice with multiple mixed infection of *Candida albicans* and *Escherichia*. (Table 16)

TABLE 16

Effect of PL-18 (SEQ ID NO: 1) injection takes on survival time of the mice with multiple mixed infection of *Candida albicans* and *Escherichia* (n = 20)

| Groups | Number of animals | Drugs | Dosage (mg/kg) | Mortality of mice in different days after infection | | | | | Mean survival time (day) |
|---|---|---|---|---|---|---|---|---|---|
| | | | | 1 | 2 | 3 | 4 | 5 | |
| Blank control | 20 | Normal saline | — | 0 | 0 | 0 | 0 | 0 | — |
| Negative control | 20 | — | — | 8 | 7 | 3 | 2 | 0 | 2.0 |
| Levofloxacin | 20 | Ofloxacin | 30 | 8 | 6 | 2 | 0 | 0 | 3.9* |
| PL-18(high) (SEQ ID NO: 15) | 20 | PL-18 (SEQ ID NO: 1) | 5 | 5 | 5 | 2 | 1 | 2 | 5.3** |
| PL-18(middle) (SEQ ID NO: 15) | 20 | PL-18 (SEQ ID NO: 1) | 1 | 5 | 4 | 3 | 2 | 0 | 5.7** |
| PL-18(low) (SEQ ID NO: 15) | 20 | PL-18 (SEQ ID NO: 1) | 0.2 | 4 | 4 | 5 | 2 | 2 | 4.4* |

Note:
Comparing with negative control group
*P < 0.05.
**Comparing with negative control group
**P < 0.01.

Experimental result of multiple mixed infections shows that during the fourteen-day observation, all the 20 mice from negative control group died within four days after these models are made (20/20). Mice from high, middle and low dosage groups survived with different number: average survival time of high dosage group is 5.3 d, average survival time of low dosage group is 4.4 d, average survival time of middle dosage group is 5.7 d, all these are superior to Ofloxacin positive control group.

It is known from Table 16 that average survival days of mice among PL-18 (SEQ ID NO: 1) middle dose group, PL-18 high dose group and negative control group are extremely different (p<0.01). This demonstrates that high and middle dose of PL-18 (SEQ ID NO: 4-51) have good effect on resisting on multiple mixed infection. Differences of mice average survival time among low dose PL-18 (SEQ ID NO: 1) group, Levofloxacin control group and negative control group are significant (P<0.05). This demonstrates that low dose PL-18 (SEQ ID NO: 1) group and Levofloxacin control group have the same anti-infection effect, but middle dose group is superior to high dose group obviously. Overall, 1 mg/kg dosage PL-18 (SEQ ID NO: 1) injection has the best curative effect on mice with multiple mixed infection.

Example 10

Preparation Artwork of 1 mg/Dosage Water Injection (2 ml:1 mg) of PL-18 (SEQ ID NO: 1) and Antimicrobial Peptides Series Ingredients:

| PL-18 (SEQ ID NO: 1) or other antimicrobial peptides | 1 g |
|---|---|
| Ethylenediamine tetraacetic acid disodium | 3.5 g |
| Water for injection | 2000 ml |
| Finished product | 1000 dosages |

Add 60% of water for injection into PL-18 (SEQ ID NO: 1) or other antimicrobial peptides, and stir them to be dissolved. Stir and dissolve prescribed PL-18 (SEQ ID NO: 1) or other antimicrobial peptides in 60% of total volume of prescribed water for injection. Add 0.1% concentration needle with activated carbon into the solution, heat to 50° C., stir and adsorb for thirty minutes, filter and decarbonize, and add the rest of water for injection to total volume. Sterilize and filter. Fill the solution into bottles after intermediates tested qualified. Put the filling semi-finished products in sterilization cabinet. Sterilization is conducted at 105° C. for thirty minutes Package the sterilized products after light inspection qualified to obtain final products.

Example 11

Preparation of 1 mg/Dosage Freeze-Dried Powder Injection of PL-18 (SEQ ID NO: 1), Etc.

Ingredients:

| PL-18 (SEQ ID NO: 1) or other antimicrobial peptides | 1 g |
|---|---|
| Mannitol | 300 g |
| Water for injection | 2000 ml |
| Finished product | 1000 dosages |

Add 60% of water for injection into Mannitol and stir them to be dissolved. Stir and dissolve prescribed mannitol in 60% of total volume of prescribed water for injection. Then stir and dissolve PL-18 (SEQ ID NO: 1) in the solution. Add 0.05% concentration needle with activated carbon into the solution, stir and absorb for thirty minutes, decarbonize and filter. Add the rest water for injection into the solution. Sterilizing and filtering, extraneous material can be found. Only when it's tested qualified, the solution can be filled into bottles and freeze-dried (quick freezing method). Switch on the block installation in vacuum condition, press the block severely, and take them out. The bottles are covered after the frost-like powder melted. Package the bottles after visual inspection qualified.

Example 12

Preparation of 3 mg/Piece Tablet of PL-13 (SEQ ID NO: 1) and Antimicrobial Peptides Series Ingredients:

| | |
|---|---|
| PL-13 (SEQ ID NO: 1) or other antimicrobial peptides | 3 g |
| Microcrystalline Cellulose | 75 g |
| L-hydroxypropyl Cellulose | 75 g |
| Sodium Carboxymethyl Starch | 40 g |
| Polyvinyl pyrrolidone | moderate amount |
| Alcohol | moderate amount |
| Magnesium Stearate | 1 g |
| Finished product | 1000 pieces |

Mix 3 g PL-13 (SEQ ID NO: 1) or other antimicrobial peptides, 75 g excipient Microcrystalline Cellulose, 75 g L-hydroxypropyl Cellulose and 30 g Sodium Carboxymethyl Starch evenly. Mix them with PL-13 (SEQ ID NO: 1) or other antimicrobial peptides evenly with equal increments method. Taking solution made of 5% concentration Polyvidone and 50% concentration alcohol as adhesive, make particles with granulating technique of fluidization spray. Add in 10 g Sodium Carboxymethyl Starch and 1 g Magnesium Stearate. The final products are manufactured by mixing evenly and tabletting.

Example 13

Preparation Artwork of 10 ml/Bottle Spray of PL-18 (SEQ ID NO: 1) or Antimicrobial Peptides Series Ingredients:

| | |
|---|---|
| PL-18 (SEQ ID NO: 1) or other antimicrobial peptides | 10 g |
| Disodium hydrogen phosphate | 276 g |
| Citric Acid | 129 g |
| Mannitol | 100 g |
| Water for injection | moderate amount |
| Finished product | 1000 bottles |

PL-18 (SEQ ID NO: 1) or other antimicrobial peptide are added into 40% of total volume of prescribed water for injection, and stirred to be dissolved. Mannitol, Disodic phosphate and Citric Acid are added into the solution above, and stirred to be dissolved. The rest of water for injection is added into the solution to complement the volume. Filter them with 0.2 um filter membrane and test the intermediate. Fill the solution into bottles after tested qualified. Package the bottles after full checking.

Example 14

10 mg/Pill Capsule of PL-18 (SEQ ID NO: 1) or Antimicrobial Peptides Series (0.3 g/Pill)

Ingredients:

| | |
|---|---|
| PL-18 (SEQ ID NO: 1) or antimicrobial peptides series | 10 g |
| Starch | 100 g |
| Gum Acacia | 90 g |
| Sodium carboxymethylcellulose | 90 g |
| Talc Powder | 7 g |
| Magnesium Stearate | 3 g |
| Finished product | 1000 pills |

Sift raw materials and excipients with 100 mesh respectively. 12% concentration starch paste is made of 10 g starch. All the raw materials and excipients except Talc Powder and Magnesium Stearate are mixed evenly, with starch paste added, sifted with 40 mesh, and dried at temperature between 55° C. to 60° C. Sift dried drops with 40 mesh. Mix them with Talc Powder and Magnesium Stearate evenly, and put them into capsule to obtain final products.

Example 15

10 mg/Bottle Oral Solution of PL-34 (SEQ ID NO: 6), Etc. (10 g/Bottle)

Ingredients:

| | |
|---|---|
| PL-34 (SEQ ID NO: 6) 1 | 0 g |
| Sucrose | 2000 g |
| Ethylparaben | 100 g |
| Water for injection | 10000 g |
| Finished product | 1000 bottles |

Sucrose is dissolved in 50% of total volume of prescribed water for injection. PL-34 (SEQ ID NO: 6) or other antimicrobial peptides are dissolved in 20% of total volume of prescribed water for injection, and are mixed with Sucrose solution evenly. Ethylparaben is dissolved in 10% of total volume of prescribed water for injection which has been heated to 60° C., and stirred well. Add them into sucrose solution, and mix evenly. Filter and sterilize with 0.2 um microporous membrane. Fill them into bottles after tested qualified to obtain final products.

Example 16

0.5 mg/g Ointment of PL-13 (SEQ ID NO: 1) or Other Antimicrobial Peptides (5 g/Piece)

Ingredients:

| | |
|---|---|
| PL-13 (SEQ ID NO: 1), etc. | 0.1 g |
| Macrogol 4000 | 480 g |
| Macrogol 400 | 320 g |
| Azone | 10 g |
| Tween 80 | 15 g |
| Water for injection | 175 g |
| Finished product | 1000 g |

Macrogol 4000 and Macrogol 400 are heated to 60° C. in thermostat-controlled water-bath, and stirred well. Azone is mixed with Tween 80 evenly, and then they are added into Macrogol solution to be stirred well and preserved at room temperature. PL-13 (SEQ ID NO: 1), etc. is dissolved in water for injection, and stirred with Macrogol mixture with equal increments method. Fill them into tubes after tested qualified to obtain final products.

Example 17

1 mg/g Cream of PL-18 (SEQ ID NO: 1), Etc. (5 g/Piece)

Ingredients:

| | |
|---|---|
| PL-18 (SEQ ID NO: 1), etc. | 1 g |
| Stearin | 35 g |
| Stearic Acid | 120 g |
| Liquid Paraffin | 60 g |
| White Vaseline | 10 g |
| Lanolin | 50 g |
| Triethanolamine | 4 ml |
| Ethyl Hydroxybenzoate | 1 g |
| Distilled Water | moderate amount |
| Finished product | 1000 g |

The prescribed oil phase ingredients (including Stearin, Stearic Acid, Liquid Paraffin, Vaseline, and Lanolin) are heated to 80° C. and keep warm. Raw materials are added into water phase ingredients (Triethanolamine and Ethyl Hydroxybenzoate dissolved in distilled water), stirred well and heated to 80° C. Add oil phase mixture into water phase mixture and stir them to be cream. Preserve them to be room temperature and fill them into tubes. The finished product is got.

Example 18

5 mg/Piece Gel of PL-18 (SEQ ID NO: 1), Etc. (5 g/Piece)

Ingredients:

| | |
|---|---|
| PL-18 (SEQ ID NO: 1), etc. | 1 g |
| Carbomer 940 | 10 g |
| Propylene Glycol | 200 g |
| Glycerol | 100 g |
| Trolamine | moderate amount |
| Water for injection | 680 g |
| Finished product | 1000 g |

The prescribed Glycerol, Propylene Glycol and Carbomer 940 are fully emulsified to be wet. 300 g water for injection is added into the mixture above to make it swelling. Stir them to make them mixed evenly. Trolamine is added into the mixture to make it become gel. The prescribed raw materials are dissolved in the rest of water for injection, added into gel substance and stirred well. Fill them into bottles after tested qualified. The finished product is got.

Example 19

5 mg/Bottle Eye Drops of PL-18 (SEQ ID NO: 1), Etc. (5 ml/Bottle)

Ingredients:

| | |
|---|---|
| PL-18 (SEQ ID NO: 1), etc. | 1 g |
| Ethylenediamine tetraacetic acid disodium | 0.2 g |
| Ethyl Hydroxybenzoate | 0.15 g |
| Methyl Hydroxybenzoate | 0.1 g |
| Water for injection | 994 ml |
| Finished product | 1000 ml |

20% of prescribed water for injection is heated to 60° C., with prescribed Ethyl Hydroxybenzoate and Methyl Hydroxybenzoate added. Stir them to be dissolved and preserve to room temperature. The prescribed raw materials and Ethylenediamine tetraacetic acid disodium are dissolved in 60% of prescribed water for injection and stirred well. Mix them with Ethyl Hydroxybenzoate and Methyl Hydroxybenzoate solution, put the rest of water for injection into the mixture and stir until smooth. Filter and sterilize with microporous membrane. Fill them into bottles after tested qualified. The finished product is got.

Example 20

50 mg/Bottle Aerosol of PL-26 (SEQ ID NO: 9), Etc. (20 g/Bottle)

Ingredients:

| | |
|---|---|
| PL-26 (SEQ ID NO: 9), etc. | 2.5 g |
| Laurocapram | 1 g |
| Tween 80 | 1.5 g |
| Ethyl Hydroxybenzoate | 1 g |
| Water for injection | 994 ml |
| Finished product | 1000 ml |

Raw materials are dissolved in 60% of prescribed water for injection and stirred well. Ethyl Hydroxybenzoate is dissolved in 10% of prescribed water for injection which has been heated to 60° C. Mix raw materials solution with Ethyl Hydroxybenzoate solution. Add evenly mixed prescribed Laurocapram and Tween 80 into the mixed solution, and add in water for injection to 1000 ml. Fill them into spray bottles after tested qualified. The finished product is got.

Example 21

3 mg/Piece Patch of PL-13 (SEQ ID NO: 1), Etc.

Ingredients:

| | |
|---|---|
| PL-13 (SEQ ID NO: 1), etc. | 3 g |
| Polyacrylic Acid | 30 g |
| Glycerol | 120 g |
| Dihydroxyaluminium Aminoacetate | 1.5 g |
| Ethylenediamine tetraacetic acid disodium | 0.15 g |
| Tartaric Acid | 1 g |
| Water for injection | 220 g |
| Finished product | 1000 pieces |

Add prescribed Polyacrylic Acid into Glycerol, Dihydroxyaluminium Aminoacetate and Edathamil Disodium, and spread them well, which are called A. Raw materials are stirred and dissolved in water for injection and Tartaric Acid, and added into A slowly while stirring to make them crosslink. Spread them on the backing layer, cover on with protective membrane and solidify for twenty-four hours at room temperature. Cut them to get the finished products.

Example 22

0.5 mg/Bottle Wash of PL-13 (SEQ ID NO: 1), Etc. (50 ml/Bottle)

Ingredients:

| | |
|---|---|
| PL-13 (SEQ ID NO: 1), etc. | 0.01 g |
| Menthol | 1 g |
| Sodium Benzoate | 1 g |

-continued

| | |
|---|---|
| Water for injection | 997 ml |
| Finished product | 1000 ml |

PL-13 (SEQ ID NO: 1) and other raw materials are dissolved in 60% of prescribed water for injection and stirred well. Sodium Benzoate and Menthol are dissolved in water, added into the mixed liquor above, and added in water for solution to 1000 ml. Stir them to be dissolved totally. Fill them into bottles after tested qualified. The finished product is got.

---

The invention claimed is:

1. An antimicrobial peptide with the amino acid sequence of Ac-F-K-K-L-K-K-L-F-S-K-L-W-N-W-K-NH$_2$ (SEQ ID No. 1).

2. The antimicrobial peptide of claim 1, wherein any one L in said amino acid sequence of antimicrobial peptide is substituted by I.

3. The antimicrobial peptide of claim 1, wherein any one F in the amino acid sequence of said antimicrobial peptide is substituted by L.

4. The antimicrobial peptide of claim 1, wherein any one W in the amino acid sequence of said antimicrobial peptide is substituted L.

5. The antimicrobial peptide of claim 1, wherein said antimicrobial peptide comprises all L-enantiomers or all D-enantiomers.

6. A therapeutic composition for inhibiting a bacterial and/or fungal infection, wherein the therapeutic composition includes the antimicrobial peptide of claim 1.

7. A therapeutic composition for inhibiting a bacterial and/or fungal infection, wherein the therapeutic composition includes the antimicrobial peptide of claim 5.

8. A antibacterial agent for inhibiting a bacterial and/or fungal infection, wherein the antibacterial agent includes the therapeutic composition of claim 6.

* * * * *